(12) United States Patent
Lotter

(10) Patent No.: US 11,783,476 B2
(45) Date of Patent: Oct. 10, 2023

(54) SYSTEM AND METHOD FOR ANALYZING THREE-DIMENSIONAL IMAGE DATA

(71) Applicant: DeepHealth, Inc., Cambridge, MA (US)

(72) Inventor: William Lotter, Boston, MA (US)

(73) Assignee: DeepHealth, Inc., Cambridge, MA (US)

( * ) Notice: Subject to any disclaimer, the term of this patent is extended or adjusted under 35 U.S.C. 154(b) by 296 days.

(21) Appl. No.: 17/079,957

(22) Filed: Oct. 26, 2020

(65) Prior Publication Data
US 2021/0125334 A1 Apr. 29, 2021

Related U.S. Application Data

(60) Provisional application No. 62/926,088, filed on Oct. 25, 2019.

(51) Int. Cl.
*G06T 7/00* (2017.01)
*G06K 9/00* (2022.01)
(Continued)

(52) U.S. Cl.
CPC ............ *G06T 7/0012* (2013.01); *A61B 6/025* (2013.01); *A61B 6/502* (2013.01); *G06N 3/045* (2023.01);
(Continued)

(58) Field of Classification Search
CPC ................. G06T 7/0012; G06T 5/40; G06T 2207/10112; G06T 2207/20084;
(Continued)

(56) References Cited

U.S. PATENT DOCUMENTS

| 6,909,795 B2 | 6/2005 | Tecotzky et al. |
| 7,072,498 B1 | 7/2006 | Roehrig et al. |

(Continued)

FOREIGN PATENT DOCUMENTS

| WO | 2013123091 A1 | 8/2013 |
| WO | 2018189551 A1 | 10/2018 |

(Continued)

OTHER PUBLICATIONS

Conant et al., Improving Accuracy and Efficiency with Concurrent Use of Aililicial Intelligence for Digital Breast Tomosynthesis, Radiology: Artificial Intelligence, 2019, 1(4):e180096, pp. 1-12.
(Continued)

*Primary Examiner* — Edward F Urban
*Assistant Examiner* — Duy Tran
(74) *Attorney, Agent, or Firm* — Quarles & Brady LLP

(57) ABSTRACT

The present disclosure provides a method for determining a malignancy likelihood score for breast tissue of a patient. The method includes receiving a plurality of two-dimensional images of the breast tissue, the two-dimensional images being derived from a three-dimensional image of the breast tissue, for each two-dimensional image, providing the two-dimensional image to a first model including a first trained neural network, and receiving a number of indicators from the first model, each indicator being associated with a two-dimensional image included in the plurality of two-dimensional images, generating a synthetic two-dimensional image based on the number of indicators and at least one of the plurality of two-dimensional images, providing the synthetic two-dimensional image to a second model including a second trained neural network, receiving a malignancy likelihood score from the second model, and outputting a report including the malignancy likelihood score to at least one of a memory or a display.

32 Claims, 12 Drawing Sheets

(51) Int. Cl.
| | |
|---|---|
| *G06K 9/32* | (2006.01) |
| *G06T 5/40* | (2006.01) |
| *G16H 50/20* | (2018.01) |
| *A61B 6/00* | (2006.01) |
| *A61B 6/02* | (2006.01) |
| *G06N 3/04* | (2023.01) |
| *G06V 20/64* | (2022.01) |
| *G06N 3/045* | (2023.01) |

(52) U.S. Cl.
CPC .............. *G06T 5/40* (2013.01); *G06V 20/647* (2022.01); *G16H 50/20* (2018.01); *G06T 2207/10112* (2013.01); *G06T 2207/20084* (2013.01); *G06T 2207/30068* (2013.01); *G06V 2201/03* (2022.01)

(58) Field of Classification Search
CPC .......... G06T 2207/30068; G16H 50/20; G06V 10/25; G06V 20/647; G06V 2201/03; A61B 6/025; A61B 6/502; G06N 3/0454
See application file for complete search history.

(56) References Cited

U.S. PATENT DOCUMENTS

| | | |
|---|---|---|
| 7,123,684 B2 | 10/2006 | Jing et al. |
| 7,333,645 B1 | 2/2008 | Mitchell et al. |
| 7,386,165 B2 | 6/2008 | Dundar et al. |
| 7,418,123 B2 | 8/2008 | Giger et al. |
| 7,430,272 B2 | 9/2008 | Jing et al. |
| 7,577,282 B2 | 8/2009 | Gkanatsios et al. |
| 7,616,801 B2 | 11/2009 | Gkanatsios et al. |
| 7,640,051 B2 | 12/2009 | Krishnan et al. |
| 7,668,352 B2 | 2/2010 | Tecotzky et al. |
| 7,672,494 B2 | 3/2010 | Doi et al. |
| 7,702,142 B2 | 4/2010 | Ren et al. |
| 7,760,853 B2 | 7/2010 | Jing et al. |
| 7,760,924 B2 | 7/2010 | Ruth et al. |
| 7,787,682 B2 | 8/2010 | Collins et al. |
| 7,831,296 B2 | 11/2010 | DeFreitas et al. |
| 7,840,046 B2 | 11/2010 | Jerebko et al. |
| 7,869,563 B2 | 1/2011 | Defreitas et al. |
| 7,889,896 B2 | 2/2011 | Roehrig et al. |
| 7,916,915 B2 | 3/2011 | Gkanatsios et al. |
| 7,949,091 B2 | 5/2011 | Jing et al. |
| 8,090,172 B2 | 1/2012 | Shinagawa et al. |
| 8,135,188 B2 | 3/2012 | Shinagawa et al. |
| 8,139,832 B2 | 3/2012 | Kshirsagar |
| 8,155,421 B2 | 4/2012 | Ren et al. |
| 8,175,219 B2 | 5/2012 | Defreitas et al. |
| 8,223,916 B2 | 7/2012 | Srinivas et al. |
| 8,285,020 B2 | 10/2012 | Gkanatsios et al. |
| 8,331,636 B2 | 12/2012 | Shinagawa et al. |
| 8,340,388 B2 | 12/2012 | Rosenstengel |
| 8,416,915 B2 | 4/2013 | Jing et al. |
| 8,452,379 B2 | 5/2013 | DeFreitas et al. |
| 8,565,372 B2 | 10/2013 | Stein et al. |
| 8,565,374 B2 | 10/2013 | Defreitas et al. |
| 8,565,506 B2 | 10/2013 | Marshall et al. |
| 8,571,289 B2 | 10/2013 | Ruth et al. |
| 8,634,610 B2 | 1/2014 | Kontos et al. |
| 8,634,622 B2 | 1/2014 | Woods et al. |
| 8,712,127 B2 | 4/2014 | Ren et al. |
| 8,768,026 B2 | 7/2014 | Ren et al. |
| 8,831,171 B2 | 9/2014 | Jing et al. |
| 8,897,535 B2 | 11/2014 | Ruth et al. |
| 8,983,156 B2 | 3/2015 | Periaswamy |
| 9,042,612 B2 | 5/2015 | Gkanatsios et al. |
| 9,066,706 B2 | 6/2015 | DeFreitas et al. |
| 9,084,579 B2 | 7/2015 | Ren et al. |
| 9,095,306 B2 | 8/2015 | Gkanatsios et al. |
| 9,456,797 B2 | 10/2016 | Ruth et al. |
| 9,460,508 B2 | 10/2016 | Gkanatsios et al. |
| 9,498,175 B2 | 11/2016 | Stein et al. |
| 9,549,709 B2 | 1/2017 | DeFreitas et al. |
| 9,792,703 B2 | 10/2017 | Costa |
| 9,808,215 B2 | 11/2017 | Ruth et al. |
| 9,811,758 B2 | 11/2017 | Ren et al. |
| 9,851,888 B2 | 12/2017 | Gkanatsios et al. |
| 9,892,343 B2 | 2/2018 | Ragusa et al. |
| 10,008,184 B2 | 6/2018 | Kreeger et al. |
| 10,010,302 B2 | 7/2018 | Ruth et al. |
| 10,108,329 B2 | 10/2018 | Gkanatsios et al. |
| 10,111,632 B2 | 10/2018 | Anavi et al. |
| 10,194,875 B2 | 2/2019 | DeFreitas et al. |
| 10,242,490 B2 | 3/2019 | Karssemeijer et al. |
| 10,248,882 B2 | 4/2019 | Ren et al. |
| 10,296,199 B2 | 5/2019 | Gkanatsios et al. |
| 10,398,398 B2 | 9/2019 | Ren et al. |
| 10,413,255 B2 | 9/2019 | Stein et al. |
| 10,413,263 B2 | 9/2019 | Ruth et al. |
| 10,424,411 B2 | 9/2019 | El-Zehiry |
| 10,452,252 B2 | 10/2019 | Gkanatsios et al. |
| 10,565,707 B2 | 2/2020 | Liu et al. |
| 10,573,276 B2 | 2/2020 | Kreeger et al. |
| 10,580,137 B2 | 3/2020 | Amit et al. |
| 10,638,994 B2 | 5/2020 | DeFreitas et al. |
| 10,679,095 B2 | 6/2020 | Ren et al. |
| 10,687,776 B2 | 6/2020 | Suri et al. |
| 10,702,233 B2 | 7/2020 | Pauly |
| 10,719,223 B2 | 7/2020 | Gkanatsios et al. |
| 10,762,624 B2 | 9/2020 | Daughton et al. |
| 10,779,785 B2 | 9/2020 | Itu et al. |
| 10,905,385 B2 | 2/2021 | DeFreitas et al. |
| 10,952,692 B2 | 3/2021 | Ren et al. |
| 10,959,694 B2 | 3/2021 | Jing et al. |
| 10,978,026 B2 | 4/2021 | Kreeger et al. |
| 11,096,644 B2 | 8/2021 | DeFreitas et al. |
| 11,106,950 B2 | 8/2021 | Kecskemethy et al. |
| 11,205,265 B2 | 12/2021 | Hall et al. |
| 2008/0152086 A1* | 6/2008 | Hall ................ A61B 6/5235 378/98.2 |
| 2009/0082637 A1* | 3/2009 | Galperin ............... G16H 30/20 600/300 |
| 2010/0128950 A1 | 5/2010 | Woods |
| 2014/0376690 A1 | 12/2014 | Jing et al. |
| 2018/0047211 A1* | 2/2018 | Chen ..................... G06T 19/003 |
| 2018/0075628 A1 | 3/2018 | Teare |
| 2018/0232883 A1* | 8/2018 | Sethi ..................... G16H 30/40 |
| 2018/0289347 A1 | 10/2018 | DeFreitas et al. |
| 2019/0005684 A1* | 1/2019 | De Fauw .............. G06T 11/003 |
| 2019/0090834 A1 | 3/2019 | Pauly |
| 2019/0130562 A1 | 5/2019 | Liu et al. |
| 2019/0209116 A1* | 7/2019 | Sjöstrand ............... G16H 50/30 |
| 2019/0236782 A1* | 8/2019 | Amit ..................... G06T 7/0016 |
| 2019/0318474 A1* | 10/2019 | Han ....................... A61N 5/103 |
| 2020/0348835 A1 | 11/2020 | Gkanatsios et al. |
| 2021/0128087 A1 | 5/2021 | DeFreitas et al. |
| 2021/0204894 A1 | 7/2021 | Ren et al. |
| 2022/0013089 A1 | 1/2022 | Kreeger et al. |
| 2022/0071582 A1 | 3/2022 | DeFreitas et al. |

FOREIGN PATENT DOCUMENTS

| | | |
|---|---|---|
| WO | 2019104252 A1 | 5/2019 |
| WO | 2021133954 A1 | 7/2021 |

OTHER PUBLICATIONS

Geras et al., High-Resolution Breast Cancer Screening with Multi-View Deep Convolutional Neural Networks, arXiv:1703.07047, 2017, pp. 1-8.

Kooi et al., Large Scale Deep Learning for Computer Aided Detection of Mammographic Lesions, Medical Image Analysis, 2017, 35:303-312.

Lotter et al., A Multi-Scale CNN and Curriculum Learning Strategy for Mammogram Classification, arXiv:1707.06978, 2017, pp. 1-8.

Ribli et al., Detecting and Classifying Lesions in Mammograms with Deep Learning, Scientific Reports, 2018, 8:4165, pp. 1-7.

Rodriguez-Ruiz et al., Stand-Alone Artificial Intelligence for Breast Cancer Detection in Mammography: Comparison with 101 Radi-

(56) References Cited

OTHER PUBLICATIONS ologists, JNCI: Journal of the National Cancer Institute, 2019, 111(9):916-922.

Wu, K. et al., Validation of a Deep Learning Mammography Model in a Population with Low Screening Rates, arXiv:1911.00364, 2019, pp. 1-6.

Wu, N. et al., Deep Neural Networks Improve Radiologists' Performance in Breast Cancer Screening, IEEE Transactions on Medical Imaging, 2020, 39(4):1184-1194.

Yala et al., A Deep Learning Mammography-Based Model for Improved Breast Cancer Risk Prediction, Radiology, 2019, 292(1):60-66.

Haarburger et al., Multi Scale Curriculum CNN for Context-Aware Breast MRI Malignancy Classification, arXIV:1906.06058v2, Jun. 17, 2019, 8 pages.

Jung et al., Detection of Masses in Mammograms Using a One-Stage Object Detector Based on a Deep Convolutional Neural Network, PloS ONE, 2018, 13(9):e0203355, pp. 1-16.

PCT International Search Report and Written Opinion, PCT/US2020/066912, dated Mar. 15, 2021, 19 pages.

Debelee, T. G., et al. "Survey of deep learning in breast cancer image analysis." Evolving Systems 11.1 (2020): 143-163.

Harvey, H., et al. "The role of deep learning in breast screening" Current Breast Cancer Reports 11.1 (2019): 17-22.

He, K., et al. "Deep Residual Learning for Image Recognition." arXiv preprint arXiv:1512.03385 (2015).

International Searching Authority. International Search Report and Written Opinion for application PCT/US2020/057319. dated Jan. 27, 2021. 15 pages.

James, J. J., et al. "Evaluation of a computer-aided detection (CAD)-enhanced 2D synthetic mammogram: comparison with standard synthetic 2D mammograms and conventional 2D digital mammography." Clinical radiology 73.10 (2018): 886-892.

Kyono, T. et al. "MAMMO: A deep learning solution for facilitating radiologist-machine collaboration in breast cancer diagnosis." arXiv preprint arXiv:1811.02661 (2018).

Lehman, C. D., et al. "National performance benchmarks for modern screening digital mammography: update from the Breast Cancer Surveillance Consortium." Radiology 283.1 (2017): 49-58.

Lin, T-Y, et al. "Focal Loss for Dense Object Detection." arXiv preprint arXiv:1708.02002 (2017).

Mendel, K. R., et al. "Transfer learning with convolutional neural networks for lesion classification on clinical breast tomosynthesis." Medical Imaging 2018: Computer-Aided Diagnosis. vol. 10575. International Society for Optics and Photonics, 2018.

Rodriguez-Ruiz, A., et al. "Detection of breast cancer with mammography: effect of an artificial intelligence support system." Radiology 290.2 (2019): 305-314.

Svahn, T. M. "Digital Mammography and Digital Breast Tomosynthesis." Breast Cancer Screening and Diagnosis. Springer, New York, NY, 2015. 65-91.

\* cited by examiner

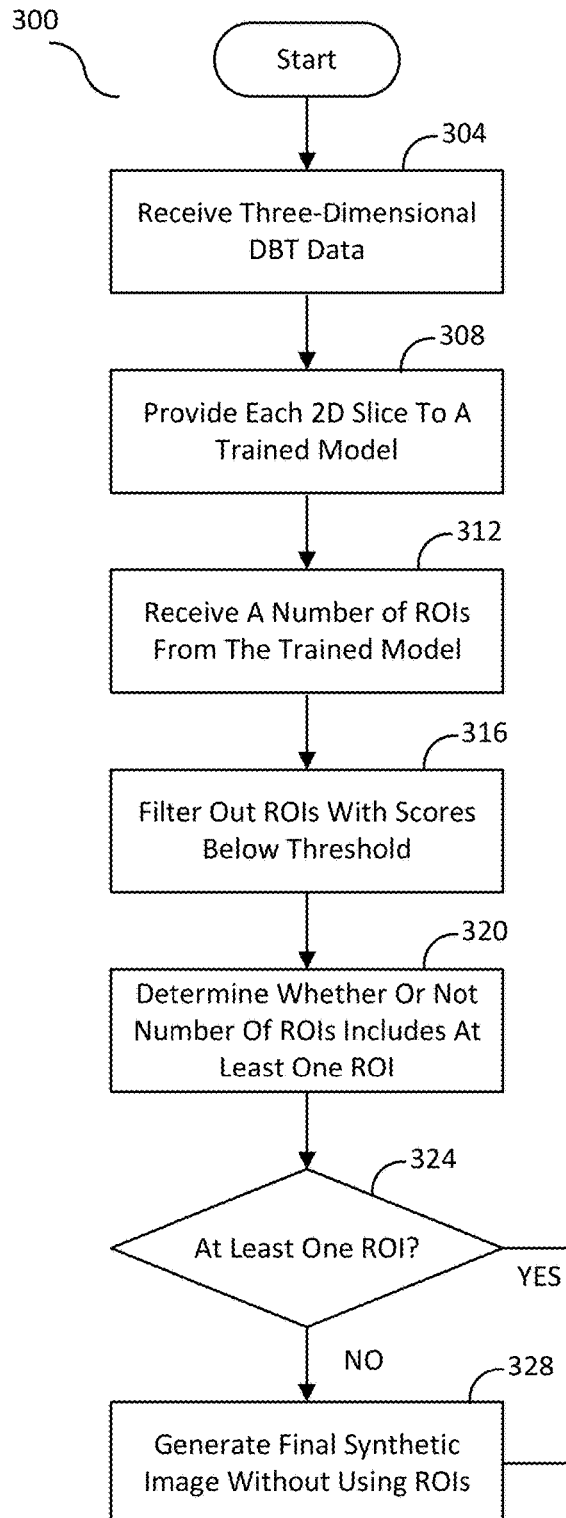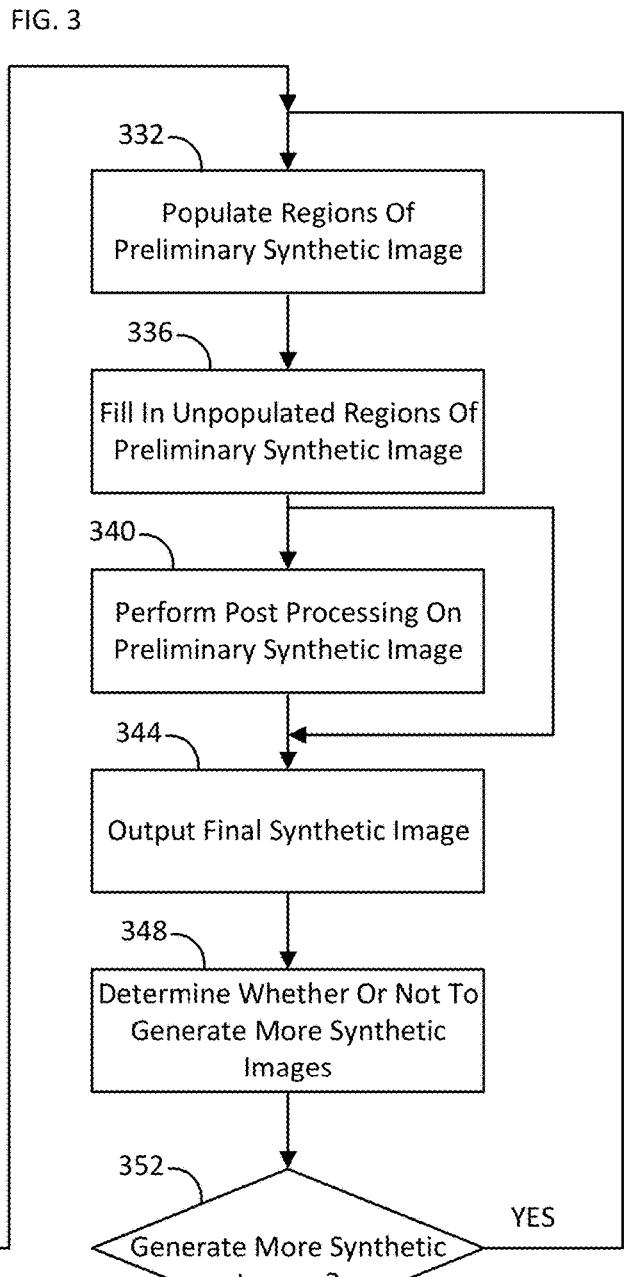
FIG. 3

SYSTEM AND METHOD FOR ANALYZING THREE-DIMENSIONAL IMAGE DATA

CROSS REFERENCE TO RELATED APPLICATIONS

This application claims the benefit of priority to U.S. Provisional Patent Application No. 62/926,088, filed Oct. 25, 2019, the contents of which are incorporated herein by reference in its entirety.

STATEMENT REGARDING FEDERALLY SPONSORED RESEARCH

Not applicable.

BACKGROUND

Digital breast tomosynthesis (DBT), which may also be referred to as three-dimensional (3D) mammography, has been demonstrated to have superior clinical performance in detecting breast cancer than traditional full-field digital mammography. Full-field mammography may generate a two-dimensional (2D) projection image representing the entire depth of the breast for a number of views. In contrast, DBT may generate 10-150 or more 2D images representing thin slices (i.e., ~1 mm thick) of the breast per view.

Because DBT generates more data than full-field mammography, it can be difficult for a human practitioner to sift through the DBT-generated images and make a determination whether or not malignant tumors and/or lesions are present. Additionally, what is and is not considered a potentially malignant region may vary from practitioner to practitioner, which can lead to inconsistent determinations of if a patient has malignant tumors and/or lesions, even using the same set of images.

Thus, it would be desirable to have systems and methods that more efficiently and accurately analyze 3D mammography data, as well as uniformly estimate malignant tumors and/or lesions using 3D mammography data.

SUMMARY

The present disclosure provides systems and methods for efficiently and accurately analyzing 3D mammography data, as well as uniformly estimating malignant tumors and/or lesions using 3D mammography data. In one non-limiting aspect, the present disclosure provides a method for determining a malignancy likelihood score for breast tissue of a patient. The method includes receiving a plurality of two-dimensional images of the breast tissue, the two-dimensional images being derived from a three-dimensional image of the breast tissue, for each two-dimensional image, providing the two-dimensional image to a first model including a first trained neural network, and receiving a number of indicators from the first model, each indicator being associated with a two-dimensional image included in the plurality of two-dimensional images, generating a synthetic two-dimensional image based on the number of indicators and at least one of the plurality of two-dimensional images, providing the synthetic two-dimensional image to a second model including a second trained neural network, receiving a malignancy likelihood score from the second model, and outputting a report including the malignancy likelihood score to at least one of a memory or a display.

In the method, the indicator can include a relevancy score, and the generating may include determining that a first indicator and a second indicator overlap, determining that the first indicator has a higher relevancy score than the second indicator, and, in response to determining the first indicator has a higher relevancy score, including at least a portion of the first indicator in the synthetic two-dimensional image. The first indicator may be associated with a first two-dimensional image included in the plurality of two-dimensional images and the second indicator may be associated with a second two-dimensional image included in the plurality of two-dimensional images.

In the method, each indicator may include an array of pixels, each pixel including an intensity value, and a relevancy score.

In the method, the generating may include setting a first intensity value included in a first pixel included in the synthetic two-dimensional image equal to a second intensity value included in an indicator.

In the method, the generating may include setting a first intensity value included in a first pixel included in the synthetic two-dimensional image equal to a second intensity value included in a second two-dimensional image included in the plurality of two-dimensional images, the second intensity value being included in a second pixel not associated with any indicator.

In the method, the second two-dimensional image may be associated with at least one indicator.

In the method, the generating may include determining a first coverage area associated with a first indicator included in the number of indicators and including a second array of pixels, determining a second coverage area associated with a second indicator included in the number of indicators and including a third array of pixels, and determining a first intensity value of a first pixel included in the synthetic two-dimensional image based on a second intensity value included in the first coverage area and a third intensity value included in the second coverage area. The first coverage area can include at least one pixel not included in the first indicator and the second coverage area can include at least one pixel not included in the second indicator. The determining the first intensity value of the first pixel can include setting the first intensity value equal to the sum of the second intensity value multiplied by a first weight plus the third intensity value multiplied by a second weight.

In the method, the generating can include determining that a first indicator and a second indicator overlap, determining that the first indicator has a higher relevancy score than the second indicator, and in response to determining the first indicator has a higher relevancy score, not including any portion of the second indicator in the synthetic two-dimensional image.

In the method, the three-dimensional image can be generated using digital breast tomosynthesis.

In the method, the first trained neural network can include a first subnetwork, and the second trained neural network can include a second subnetwork, the first subnetwork and the second subnetwork including the same number of layers and filters. The second trained neural network can be trained using a set of weight values of the first neural network as initial weight values.

The method can further include removing at least one indicator from the number of indicators, and generating a second synthetic two-dimensional image based on the number of indicators and at least one of the plurality of two-dimensional images.

In the method, the first model can be trained based on an image dataset comprising two-dimensional full-field digital mammography images annotated by a medical practitioner.

In the method, each two-dimensional image included in the plurality of two-dimensional images of the breast tissue can be a slice included in a three-dimensional digital breast tomosynthesis volume.

In another non-limiting aspect, the present disclose provides a method for generating a synthetic two-dimensional image for breast tissue of a patient. The method includes receiving a plurality of two-dimensional images of the breast tissue, the two-dimensional images being derived from a three-dimensional image of the breast tissue, for each two-dimensional image, providing the two-dimensional image to a model including a trained neural network, and receiving a number of regions of interest from the model, each region of interest including a score and being associated with a two dimension image included on the plurality of two-dimensional images, determining a target region of interest has a highest score of any region of interest in the number of regions of interest at least partially overlapping a two-dimensional location of the target region of interest, the two-dimensional location being shared by each of the plurality of two-dimensional images, and generating a synthetic two-dimensional image based on the target region of interest and at least one of the plurality of two-dimensional images.

In the method, each region of interest can further include an array of pixels, each pixel including an intensity value.

In the method, the generating can include setting a first intensity value included in a first pixel included in the synthetic two-dimensional image equal to a second intensity value included in a region of interest.

In the method, the generating can include setting a first intensity value included in a first pixel included in the synthetic two-dimensional image equal to a second intensity value included in a second two-dimensional image included in the plurality of two-dimensional images, the second intensity value being included in a second pixel not associated with any region of interest.

In the method, the generating can include determining a first coverage area associated with a first region of interest included in the number of region of interests and including a second array of pixels, determining a second coverage area associated with a second region of interest included in the number of region of interests and including a third array of pixels, and determining a first intensity value of a first pixel included in the synthetic two-dimensional image based on a second intensity value included in the first coverage area and a third intensity value included in the second coverage area. The first coverage area can include at least one pixel not included in the first region of interest and the second coverage area can include at least one pixel not included in the second region of interest. The determining the first intensity value of the first pixel can include setting the first intensity value equal to the sum of the second intensity value multiplied by a first weight plus the third intensity value multiplied by a second weight.

In the method, the generating can include determining that a first region of interest and a second region of interest overlap, determining that the first region of interest has a higher relevancy score than the second region of interest, and in response to determining the first region of interest has a higher relevancy score, not including any portion of the second region of interest in the synthetic two-dimensional image.

In the method, the three-dimensional image can be generated using digital breast tomosynthesis.

The method may further include removing at least one region of interest from the number of region of interests and generating a second synthetic two-dimensional image based on the number of region of interests and at least one of the plurality of two-dimensional images.

In yet another non-limiting aspect, the present disclosure provides a system for determining a malignancy likelihood score for breast tissue of a patient. The system includes a memory configured to store a plurality of two-dimensional images of the breast tissue, the two-dimensional images being derived from a three-dimensional image of the breast tissue, a processor configured to access the memory and to provide each two-dimensional image to a first model including a first trained neural network, and receive, for each two-dimensional image, a number of indicators from the first model, each indicator being associated with a two-dimensional image included in the plurality of two-dimensional images, generate a synthetic two-dimensional image based on the number of indicators and at least one of the plurality of two-dimensional images, provide the synthetic two-dimensional image to a second model including a second trained neural network, determine a malignancy likelihood score using the second model, and a display configured to display a report including the malignancy likelihood score.

In the method, the model can be trained based on an image dataset comprising two-dimensional full-field digital mammography images annotated by a medical practitioner. In the method, each two-dimensional image included in the plurality of two-dimensional images of the breast tissue can be a slice included in a three-dimensional tomosynthesis volume.

In an additional non-limiting aspect, the present disclosure provides a system for generating a synthetic two-dimensional image for breast tissue of a patient. The system includes a memory configured to store a plurality of two-dimensional images of the breast tissue, the two-dimensional images being derived from a three-dimensional image of the breast tissue, a processor configured to access the memory and to provide each two-dimensional image to a model including a trained neural network, and for each two-dimensional image, receive a number of regions of interest from the model, each region of interest including a score and being associated with a two dimension image included on the plurality of two-dimensional images, determine a target region of interest has a highest score of any region of interest in the number of regions of interest at least partially overlapping a two-dimensional location of the target region of interest, the two-dimensional location being shared by each of the plurality of two-dimensional images, and generate a synthetic two-dimensional image based on the target region of interest and at least one of the plurality of two-dimensional images.

In a further non-limiting aspect, the present disclosure provides a system for determining a malignancy likelihood score for breast tissue of a patient. The system includes a memory configured to store a plurality of two-dimensional images of the breast tissue, the two-dimensional images being derived from a three-dimensional image of the breast tissue, a processor configured to access the memory and to provide each two-dimensional image to a first model comprising a first trained neural network, receive, for each two-dimensional image, a number of indicators from the first model, each indicator being associated with a two-dimensional image included in the plurality of two-dimensional images, generate a first synthetic two-dimensional image based on the number of indicators and at least one of the plurality of two-dimensional images, generate a second synthetic two-dimensional image based on the first synthetic two-dimensional image and at least one of the plurality of two-dimensional images, generate a third synthetic two-dimensional image based on the first synthetic two-dimensional image and at least one of the plurality of two-dimensional images, provide the first synthetic two-dimensional image, the second synthetic two-dimensional image, and the third synthetic two-dimensional image to a second model comprising a second trained neural network, determine a malignancy likelihood score using the second model, and a display configured to display a report including the malignancy likelihood score.

In a still further non-limiting aspect, the present disclosure provides a system for generating a synthetic two-dimensional image for breast tissue of a patient. The system includes a memory configured to store a plurality of two-dimensional images of the breast tissue, the two-dimensional images being derived from a three-dimensional image of the breast tissue and each two-dimensional image being associated with a slice number, a processor configured to access the memory and to sequentially provide a first two-dimensional image, a second two-dimensional image, and a third two-dimensional image included in the plurality of two-dimensional images to a model comprising a trained neural network, a slice number associated with the first two-dimensional image and a slice number associated with the second two-dimensional image differing by a predetermined offset value, and the slice number associated with the second two-dimensional image and a slice number associated with the third two-dimensional image differing by the predetermined offset value, for each two-dimensional image included in the plurality of two-dimensional images, receive a number of regions of interest from the model, each region of interest comprising a score and being associated with a two-dimensional image included in the plurality of two-dimensional images, determine a target region of interest has a highest score of any region of interest in the number of regions of interest at least partially overlapping a two-dimensional location of the target region of interest, the two-dimensional location being shared by each of the plurality of two-dimensional images, and generate a synthetic two-dimensional image based on the target region of interest and at least one of the plurality of two-dimensional images.

BRIEF DESCRIPTION OF THE DRAWINGS

FIG. 3 is a flow chart that shows some examples of steps in a process for creating a synthetic image using a model trained to detect regions of interest in two-dimensional slices of tomosynthesis data.

DETAILED DESCRIPTION

As will be described herein, exemplary systems and method for efficiently and uniformly displaying relevant regions of three-dimensional (3D) tomography data using one or more synthesized two-dimensional (2D) images as well as determining malignancy using the one or more synthesized images using machine learning techniques are provided.

Approaches other than the systems and methods described below may exist for analyzing relevant regions of 3D tomosynthesis data and/or determining malignancy of tumors and/or lesions of breast tissue, all with drawbacks. One approach is to have a human practitioner label relevant regions of every slice included in a 3D mammogram. Human-based approaches can be costly and slow due to the extensive time taken to label each 2D slice by a human practitioner. Additionally, human-based approaches can be inconsistent due to differing preferences/expertise levels between human practitioners.

Another approach is to train a machine learning model that receives an entire 3D tomography dataset (i.e., every slice included in the 3D tomography dataset) and outputs a malignancy likelihood score indicating malignancy of tumors and/or lesions present in the breast tissue. This approach can be an infeasible due to the size of the data and memory limits of a data processing system, and may also be prone to overfitting.

Yet another approach may involve randomly choosing a slice from a set of 2D slices sampling or choosing a default slice (i.e., a twenty-fifth slice or middle slice) of a set of 2D slices, and training a machine learning model to output a malignancy likelihood score based on the slice. This approach may also be prone to overfitting because the slice would likely not contain a tumor and/or lesion, if present.

Figure 1:
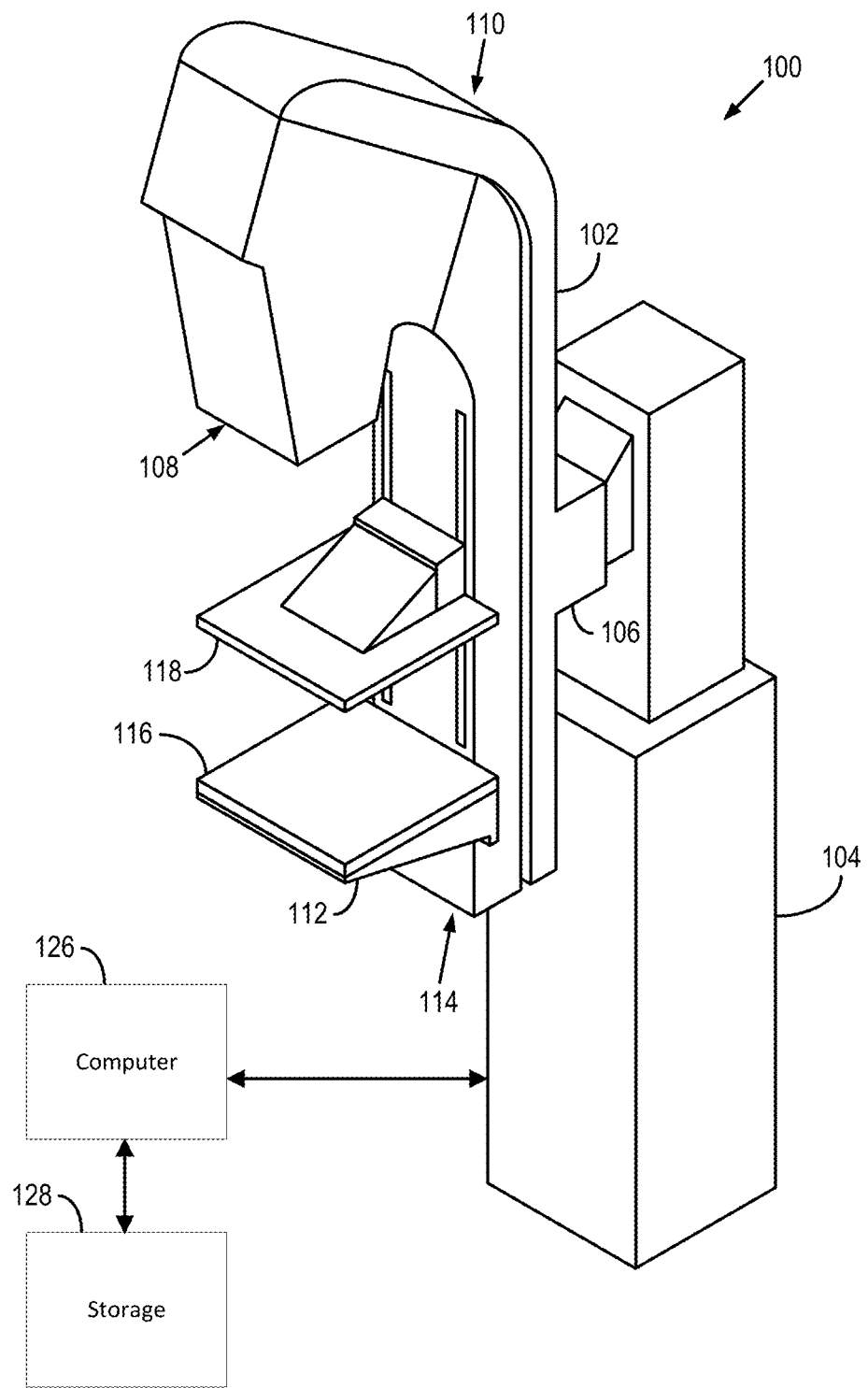
FIG. 1 is a block diagram that shows an exemplary x-ray imaging system.

Referring to FIG. 1, an example of an x-ray imaging system 100, such as a 3D digital breast tomosynthesis (DBT) system, is shown. The x-ray imaging system 100 can include an x-ray source assembly 108 coupled to a first end 110 of an arm 102. An x-ray detector assembly 112 can be coupled proximate an opposing end 114. The x-ray source assembly 108 may extend substantially perpendicular to the arm 102 and be directed toward the x-ray detector assembly 112. The x-ray detector assembly 112 also extends from the arm 102 such that the x-ray detector assembly 112 receives x-ray radiation produced by the x-ray source assembly 108, transmitted through the breast, and incident on the x-ray detector assembly 112. A breast support plate 116, and a breast compression plate 118, are positioned between the x-ray source assembly 108 and the x-ray detector assembly 112. The x-ray source assembly 108 may be stationary or movable. The x-ray imaging system 100 can generate a reconstructed image including 3D DBT data. The 3D DBT data can include a number of 2D slices. In some embodiments, the reconstructed image can include 3D tomography data including a plurality of 2D slices having a thickness of about 1 mm. The 2D slices can be used to create a synthetic 2D image, which will be described below. In some embodiments, the x-ray imaging system 100 can generate intermediate two-dimensional "slabs," representing, for example, maximum intensity projections of a subset of 2D slices. For example, a single maximum intensity projection slab can be generated from ten slices, and multiple slabs can be generated from a plurality of slices, such as ten slabs from one hundred slices. The reconstructed image can be applied as an input to a computer 126 which stores the image in a mass storage device 128, which can include a memory. The computer 126 may also provide commands to the x-ray imaging system 100 in order to control the generation of the reconstructed image.

Figure 2:
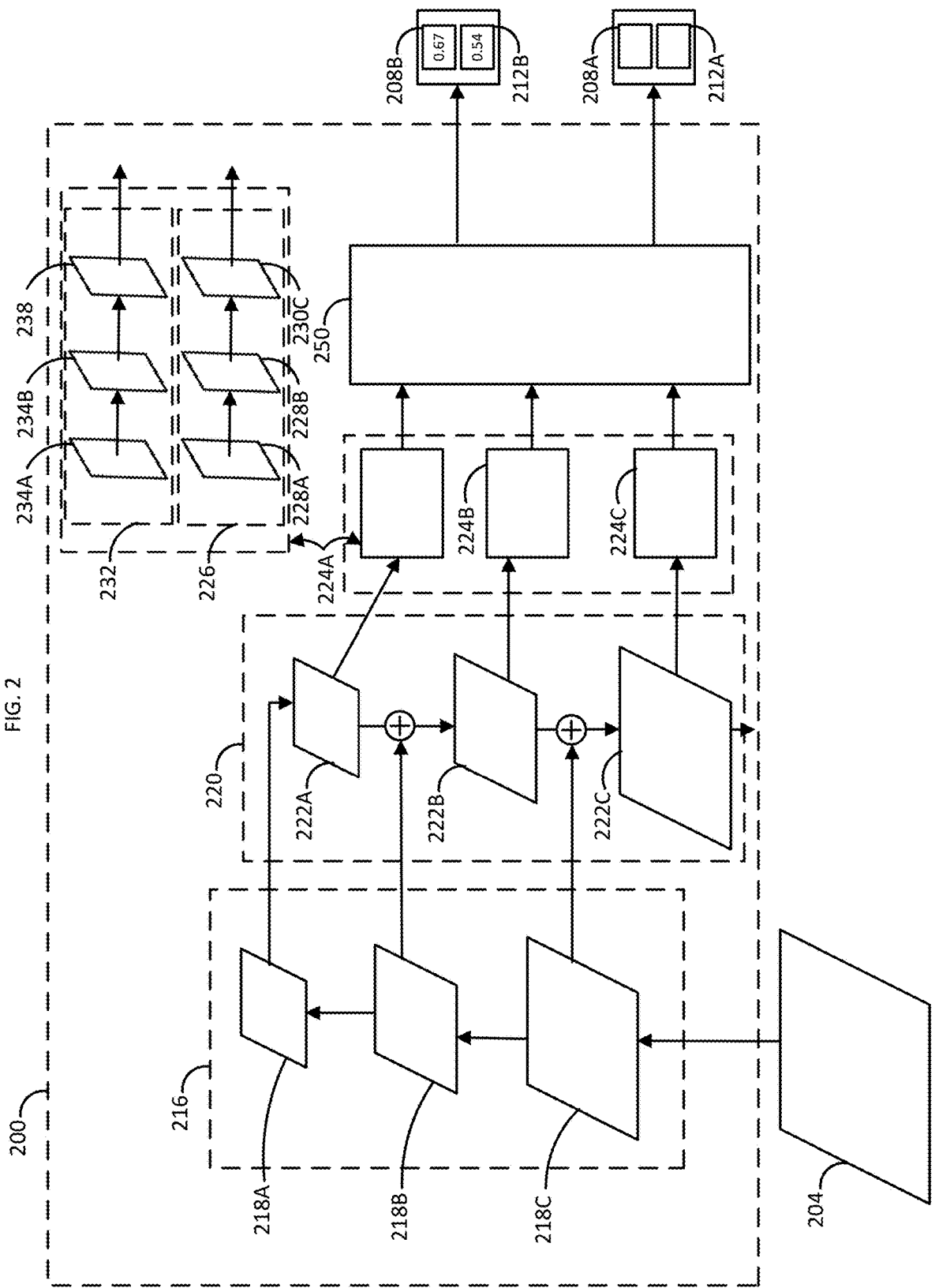
FIG. 2 is a block diagram that shows an exemplary embodiment of a model for generating regions of interest for a two-dimensional slice of three-dimensional tomosynthesis data.

Referring to FIG. 2, an exemplary embodiment of a model 200 for generating regions of interest (ROIs) for a two-dimensional (2D) slice 204 of 3D tomosynthesis data is shown. The ROIs may be referred to as indicators. The model 200 can accept the 2D slice 204 and output any number of ROIs, for example, a first ROI including a first area 208A and a first score 208B, and a second ROI including a second area 212A and a second score 212B. Each ROI can be associated with a slice number indicating the 2D slice that the ROI was generated based on, for example a fourth slice of a set of seventy-five 2D slices. The slice number can be used when selecting and/or combining ROIs to create a synthetic image, as will be explained below. Depending on the characteristics of the 2D slice 204, such as when the 2D slice 204 if deemed to not have any regions that sufficiently indicate a potential malignancy, zero ROIs may be output. Each ROI can include an area that can be a subregion of the 2D slice 204. As noted above, each 2D slice can be formatted as an array of pixels. The subregion can be a subset of the array of pixels. In some embodiments, the model 200 can include one or more neural networks configured to detect objects within 2D images. The objects can be ROIs.

In some embodiments, the model 200 can output ROI's that follow a predetermined shape. For example, rectangular bounding boxes can be used to encompass a potential candidate for a tumor or lesion. It is contemplated that irregular shapes (e.g., a "blob" of pixels) can be used to better outline potential tumors or lesions. When creating a training database of ROIs, one or more human practitioners may find it more intuitive to use rectangular bounding boxes than other shapes. Neural networks that use segmentation mask-based approaches to identify objects could be used to output predicted ROIs with irregular shapes. The model 200 can then be trained to identify rectangular-shaped ROIs including a subarray of the pixels included in the 2D slice 204. The pixels of the ROI can include one or more color intensity values (e.g., a white intensity value) and a location within the 2D slice 204 (e.g., the pixel at a given (x, y) location in a 2000×1500 pixel slice). While some mammography imaging systems produce greyscale images of breast tissue, it is appreciated that the model can be used with colorized 2D slices. Each 2D slice of 3D tomosynthesis data can be the same size, such as 2000×1500 pixels.

In addition to the subarray of pixels, the ROI can include a relevancy score indicating how relevant the subarray of pixels is to determining a malignancy likelihood score (which will be explained below in conjunction with FIG. 7). The relevancy score can be used to create a synthetic 2D image using one or more ROIs, as will be explained in detail below. The relevancy score can be selected from a range of values such as between 0 and 1. When identifying ROIs for a training dataset, a human practitioner can assign relevancy scores for each ROI within the range of the values. The human practitioner could alternatively assign relevancy scores using a different scale, such as 0-100 (with higher scores indication higher potential for malignancy) which could then be normalized to relevancy score range used by the model 200. In some embodiments, the human practitioner can identify ROIs as benign in order to better train the model 200 to identify potentially malignant ROIs.

In some embodiments, the model 200 can include a neural network such as a convolutional neural network. In order to train the model 200, a training dataset including 2D data consisting of full-field digital mammography (FFDM) images and/or slices from a set of 3D tomosynthesis images and pre-identified (e.g., by one or more medical practitioners) ROIs can be used to train the model. Human practitioners can identify ROIs by examining a given 2D image, outlining, using a predetermined shape such as a rectangular box, any regions that may be of interest, and assign a relevancy score to the predetermined shape based on their medical expertise and/or experience in evaluating tumors and/or lesions. Alternatively, the relevancy score can be assigned based on pathology results that indicate whether or not a lesion is malignant. A large training database can be generated by having one or more medical practitioners identify (e.g., annotate) ROIs in 2D images taken from a plurality of FFDM images or slices of 3D tomosynthesis images (e.g., images of multiple patients). An advantage of using FFDM images is that there are presently more publicly available annotated FFDM images than annotated 3D tomosynthesis images. Additionally, 2D images are easier to annotate than 3D tomosynthesis images, which can require annotating a large number of individual slices included in each 3D tomosynthesis image. Once trained, the model 200 can receive an input 2D slice and output one or more ROIs, each ROI including an estimated relevancy score and a subarray of pixels of the input 2D slice.

The model 200 can include a number of layers such as convolutional layers. It is understood that some embodiments of the model 200 may have different numbers of layers, a different arrangement of layers or other differences. However, in all embodiments, the model 200 can be capable of receiving an input 2D input slice and outputting any regions of interest associated with the input 2D input slice. The model 200 can be a one-stage detection network including one or more subnetworks.

The model 200 can include a first subnetwork 216. The first subnetwork 216 can be a feedforward residual neural network ("ResNet") with one or more layers 218A-C. A second subnetwork 220 can be built on top of the first subnetwork to effectively create a single neural network, using the first subnetwork 216 as the backbone for the network. The second subnetwork 220 can contain a plurality of layers including a first layer 222A, a second layer 222B, and a third layer 222C, though other numbers of layers (i.e., five layers) can be used, and three layers are shown for simplicity. Each of the first layer 222A, the second layer 222B, and the third layer 222C can be a convolutional layer. Each layer can be made of a number of building blocks (not shown). Each building block can include a number of parameters layers such as three parameter layers, each parameter layer including a number of filters (e.g., 256) with a given filter size (e.g., 3×3). Each of the first layer 222A, the second layer 222B, and the third layer 222C can have an associated output size such as 144×144, 72×72, and 36×36. The output sizes can vary between input slices based on pre-processing conditions and/or parameters. As the output size decreases between layers of the second subnetwork 220, the number of filters of the parameter layers can increase proportionally, i.e., halving output size results in doubling the number of filters. The second subnetwork can also include a global average pooling layer connected to a final layer (i.e., the third layer 222C), a fully-connected layer connected to the global average pooling layer, and a softmax layer connected to the fully-connected layer and having a 1×1 output size (i.e., a single value).

The model 200 can include a plurality of tertiary subnetworks such as a first tertiary network 224A, a second tertiary network 224B, and a third tertiary network 224C. Each of the tertiary networks 224A-C can be connected to a layer of the second subnetwork 220. The first tertiary network 224A can be connected to the first layer 222A, the second tertiary network 224B can be connected to the second layer 222B, and the third tertiary network 224C can be connected to the third layer 222C. Each tertiary network can receive features from a layer of the second subnetwork 220 in order to detect tumors and/or lesions at different levels of scale.

Each tertiary network can include a box regression subnetwork 226. The box regression subnetwork 226 can include one or more convolutional layers 228A-B, each followed by rectified linear (ReLU) activations, and a final convolutional layer 230 configured to output regression coordinates corresponding to anchors associated with a portion of one of the layers of the second subnetwork 220 (and corresponding to an array of pixels of the input 2D slice 204). The anchors can be predetermined subarrays of the various layers of the second subnetwork 220. The regression coordinates can represent a predicted offset between an anchor and a predicted bounding box. For each bounding box included in an ROI, a set of regression coordinates (e.g. four regression coordinates) and the corresponding anchor can be used to calculate the coordinates of the bounding box.

Each tertiary network can include a classification subnetwork 232. The classification subnetwork 232 can include one or more convolutional layers 234A-B, each followed by ReLU activations, and a final convolutional layer 238 followed by sigmoidal activations to output predictions of object presence (i.e., malignant tumor and/or lesion presence). The classification subnetwork 232 can be used to obtain one or more estimations of whether or not a patient has a malignant tumor and/or lesion at various spatial locations of the 2D slice 204. More specifically, each bounding box can be associated with an estimated score output by the classification subnetwork. In some embodiments, the value of each estimated score can range from zero to one. One of the spatial locations can include an entire layer, i.e., first layer 222A, of the second subnetwork 220. In this way, the classification subnetwork 232 can output an estimation of whether or not a patient has a malignant tumor and/or lesion based on a 2D slice. It is contemplated that the final convolutional layer 238 can be followed by Softmax activations in models that are trained to classify multiple types of malignant regions, for example multiple levels of malignancy (e.g., low risk regions, high risk regions, etc.).

The model 200 can include an output layer 250 for normalizing data across different scales, calculating bounding box coordinates, and filtering out low scoring bounding box predictions. The output layer 250 can receive outputs from the tertiary subnetworks 224A-C and output one or more ROIs, each ROI including an array of pixels scaled to the array size of the 2D slice 204 and an associated score. The array of pixels can be a bounding box (e.g., a rectangular bounding box) calculated based on the regression coordinates and the anchors. The output layer 250 can filter out any scores below a predetermined threshold, for example, 0.5. In some embodiments, the output layer 250 can receive outputs from the tertiary subnetworks 224A-C and output a single malignancy likelihood score. In some embodiments, the single malignancy likelihood score can be selected to be the highest scoring bounding box score.

Referring to FIG. 1 as well as FIG. 3, a process 300 for creating a synthetic image using a model trained to detect ROIs in 2D slices of 3D tomosynthesis data is shown. The process 300 can include one or more steps for selecting one or more of the most relevant ROIs output from the model and using the ROIs to create the synthetic image. The process 300 can be implemented as instructions on one or more memories included in a data processing system. The data processing system can further include one or more processors in communication with the one or more memories and configured to execute the instructions. The one or more processors can be configured to access a memory, which can be included in the mass storage device 128, having 3D tomosynthesis data including a number of two-dimensional slices stored thereon.

At 304, the process 300 can receive 3D tomosynthesis data of breast tissue of a patient. The 3D tomosynthesis data can be generated by a 3D mammography imaging system such as the x-ray imaging system 100. The 3D tomosynthesis data can include a number of 2D slices corresponding to a predetermined thickness, such as 1 mm, of the breast tissue. Depending on the patient and/or imaging system, the 3D tomosynthesis data may include about 10-150 2D slices or more. Each 2D slice can be an array of pixels of a predetermined size, such as 2000×1500 pixels. The process 300 can then proceed to 308.

At 308, the process 300 can individually provide each of a number of the 2D slices to a trained model capable of detecting ROIs based on the 2D slices. The trained model can be the model 200 described above. In some embodiments, all of the 2D slices can be provided to the trained model. In some embodiments, a subset of the 2D slices, such as every fifth slice, can be provided to the trained model. The process 300 can then proceed to 312. In some embodiments, the trained model can be trained based on an image dataset including two-dimensional full-field digital mammography images annotated by a medical practitioner.

At 312, the process 300 can receive, for each 2D slice provided to the model, a number of ROIs the model outputs. The model may output zero ROIs, one ROI, or a plurality of ROIs. Depending on the 2D slices and/or the model, a majority of the slices may not have any ROIs. As described above, the ROI can include a score and a subarray of the pixels of the 2D slice, each pixel having an intensity value and a location within the 2D slice. Each ROI can be associated with a slice number indicating which 2D slice of the 3D tomosynthesis data the ROI was generated from. The process 300 can then proceed to 316.

At 316, the process 300 can filter out any ROIs that have a score below a predetermined threshold value from the number of ROIs. The threshold value can be selected in order to include more or less ROIs in a final synthetic image (by selecting a lower or higher threshold value respectively), to reduce potential false negatives (by selecting a lower value), and/or in order to reduce potential false positives (by selecting a higher value). For example, a user could select a threshold value of 0.5 if the score can range between 0 and 1. The process 300 can then remove any ROIs that have a score below 0.5 from the number of ROIs. The process 300 can then proceed to 320.

At 320, the process 300 can determine whether or not the number of ROIs contains at least one ROI. The process 300 can then proceed to 324.

At 324, the process 300 can proceed to 328 in response to determining that the number of ROIs does not include at least one ROI ("NO" at 324). Alternatively, the process 300 can proceed to 332 in response to determining that the number of ROIs includes at least one ROI.

At 328, the process 300 can generate the final synthetic image without using any ROIs. In some embodiments, the process can select a default slice of the 2D slices included in the 3D tomosynthesis data to use as the final synthetic image. The default slice may be randomly selected, a first slice of the 2D slices (e.g., the first slice of seventy-five 2D slices), a last slice of the 2D slices (e.g., the seventy-fifth slice of seventy-five 2D slices), or a middle slice of the 2D slices (e.g., the thirty-eighth slice of seventy-five 2D slices). The pixels of the default slice can then be included as the pixels of the final synthetic image.

In some embodiments, the process 300 can select a pixel with the greatest intensity value at a given pixel location (e.g., an (x,y) location in an array) in the 2D slices to be included in the final synthetic image. In other words, the process 300 can use maximum intensity projection to generate the final synthetic figure based on the 2D slices. The final synthetic image can have the same dimensions as each of the 2D slices. For each pixel location, the process 300 can determine which slice(s) has the greatest intensity value, and use the greatest intensity value at the pixel location in the final synthetic image. In this way, pixels with the highest intensity, which may correspond to potential lesions, can be included in the final synthetic image.

In some embodiments, the process 800 can average two or more intensity values from two or more 2D slices for each pixel location. The two or more 2D slices can be chosen by selecting every $x^{th}$ 2D slice (i.e., every third slice or every fifth slice), selecting the first 2D slice and the last 2D slice, other subset of the 2D slices, or every slice included in the 2D slices. The intensity values at each pixel location can then be averaged in order to provide an overview of the breast tissue.

At 332, the process 300 can populate regions of a preliminary synthetic image with one or ROIs included in the number of ROIs. The preliminary synthetic image can be an array the same size as the final synthetic image initialized with null values for each of the pixel intensity values. The process 300 can then add one or more ROIs to the preliminary synthetic image. The ROIs can be added based on one or more criteria. In some embodiments, the process can determine the ROI with the highest score for each pixel location. The intensity value of the preliminary synthetic image at the pixel location can then be set equal to the intensity value of the ROI at the pixel location. In the case that multiple ROIs have the same score at a given pixel location, the ROI with the largest number of pixels, the largest number of pixels encircling the pixel location, and/or the highest intensity value at the pixel location can be selected as the ROI for the pixel location. In some embodiments, the preliminary synthetic image can be populated based on an intersection-over-union threshold. If multiple ROIs overlap at a given pixel, the process 300 may "suppress" all the ROIs except for the highest scoring ROI by not using the lower scoring ROIs to populate the preliminary synthetic image. ROIs that are used to populate the preliminary synthetic image may be removed from the number of ROIs, and any ROIs remaining in the number of ROIs may be used to create an additional synthetic image, as will be explained below. Alternatively, the higher scoring ROIs used to populate the preliminary image can be used to populate additional synthetic images where the higher scoring ROIs do not overlap any of the low-scoring ROIs that were not used in the preliminary image. For example, ROIs with scores of 0.85 and 0.75 could be used to populate the preliminary image. The ROI with the score of 0.85 may overlap a lower scoring ROI with a score of 0.65 (e.g., occupy at least one of the same pixel locations as the ROI with a score of 0.65) and the ROI with the score of 0.75 may not overlap the ROI with a score of 0.65. An additional synthetic image can then be generated using the ROI with a score of 0.75 and the ROI with the score of 0.65. Each pixel of the preliminary synthetic image can also be associated with the slice number of the ROI used to populate the given intensity value of the given pixel. The process 300 can then proceed to 336.

At 336, the process 300 can fill in unpopulated regions of the preliminary synthetic image. In some embodiments, the process 300 can fill in the unpopulated regions using a watershed-by-flooding algorithm. To implement the watershed-by-flooding algorithm, the process 300 can populate the unpopulated regions based on the 2D slice each ROI is associated with. The process 300 can generate coverage areas for each 2D slice initialized with the pixels of the given ROI. For example, an ROI may include an array of pixels having corners at coordinates (10, 11), (50, 11), (10, 40), and (50, 40), and the process can include this array of pixels in the coverage area for the 2D slice. The process 300 can then iteratively expand the coverage area(s) until each pixel of the preliminary synthetic image is associated with a slice number, and by extension, a 2D slice. Once each pixel is associated with a 2D slice, the process 300 can, for each pixel location, set the intensity value of each pixel of the preliminary synthetic image equal to the intensity value of the pixel of the associated 2D slice at the given pixel location. The process 300 can iteratively expand each coverage area until every pixel in the preliminary synthetic image is associated with a slice number, and by extension, a 2D slice. In some embodiments, the process can expand each coverage area by one pixel upwards, downwards, leftwards, and rightwards. For example, if the coverage area includes an array of pixels having corners at coordinates (10, 11), (50, 11), (10, 40), and (50, 40), the process can expand the array to have corners at coordinates (9, 10), (51, 10), (9, 41), and (51, 41). The process 300 may cease expanding coverage areas at borders with a neighboring coverage area where further expansion of a coverage area would result in expanding the coverage area into a pixel already associated with another coverage area, or where the preliminary synthetic image ends. In cases where the process 300 would expand multiple coverage areas into the same pixel, the process 300 can expand the coverage area associated with the highest scoring ROI into the pixel. The process 300 can iteratively expand the coverage areas according to the above protocols until every pixel of the preliminary synthetic image is associated with a single coverage area, and, by extension, a single 2D slice.

In some embodiments, the process 300 can use a "slope-based" technique to fill in unpopulated regions. The process can iteratively expand coverage areas from slices for a predetermined number of iterations, then continue populating unpopulated regions using a neighboring slice until a center slice has been reached. As an example, using an ROI from slice five in a forty slice DBT volume (meaning slice twenty is the center slice), the process 300 can expand the ROI to populate unpopulated regions for a predetermined number of iterations, for example ten. Then, after the tenth iteration, the process 300 can continue populating unpopulated regions using the sixth slice. Thus, the pixels populated within a distance of ten pixels from the original ROI are included in the fifth slice, but the next ten pixels are included in the sixth slice. The process 300 can continue increasing the slice number used to populate the unpopulated regions (or decreasing, if the original slice number is higher than the middle slice, for example the thirty-sixth slice) until the middle slice number (i.e., twenty) is reached, in which case any remaining expansion comes from slice twenty. The "slope based" approach may lead to a smoother transition when two ROIs eventually touch, as well as providing a more "canonical" view of the breast. Additionally, the process 300 can adjust the spatial position of the original ROI to better match the spatial position with respect to the center slice. For example, compared to the center slice, earlier and later slices can have a breast boundary that takes up more of the image than the center slice, in which case the process can adjust the position of the ROIs in the final synthetic.

In some embodiments, the process 300 can fill in unpopulated regions of the preliminary synthetic image based on a default slice. In some embodiments, the process can select a default slice of the 2D slices included in the 3D tomosynthesis data to use to fill in unpopulated regions of the preliminary synthetic slice. The default slice may be randomly selected, a first slice of the 2D slices (e.g., the first slice of seventy-five 2D slices), a last slice of the 2D slices (e.g., the seventy-fifth slice of seventy-five 2D slices), or a middle slice of the 2D slices (e.g., the thirty-eighth slice of seventy-five 2D slices). The process 300 can associate each unpopulated pixel with the slice number of the default slice, and set the intensity values of the unpopulated pixels of the preliminary synthetic image equal to the intensity values of the pixels of the default slice at the corresponding pixel location. In some embodiments, the process 300 can set intensity values of unpopulated pixels by selecting a pixel with the greatest intensity value at a given pixel location (e.g., an (x, y) location in an array) in the 2D slices, and setting the intensity value of the unpopulated pixel equal to the greatest intensity value. In other words, the process 300 can use maximum intensity projection to fill in intensity values of unpopulated pixels based on the 2D slices. For each pixel location, the process 300 can determine which slice(s) has the greatest intensity value, associate each pixel of the preliminary synthetic image with the slice number of the 2D slice with the greatest intensity value, and set the intensity value of the unpopulated pixel equal to the greatest intensity value throughout the 2D slices at the pixel location. In this way, pixels with the highest intensity, which may correspond to potential lesions, can be included in the preliminary synthetic image.

In some embodiments, after the process 300 has generated the preliminary synthetic image, in which all pixels have been populated with an intensity value, the process 300 can proceed to 340 for post-processing of the preliminary synthetic image. In some embodiments, the process 300 can set the final synthetic image to be equal to the preliminary synthetic image, and proceed to 344.

At 340, the process 300 can perform post-processing on the preliminary synthetic image. In some embodiments, the process 300 can blend edges of the coverage areas of the preliminary image in order to potentially reduce boundary effects between coverage areas. As described above, each pixel of the preliminary image can be associated with a slice number and/or 2D slice. At regions of pixels of the preliminary image near where two coverage areas border each other, the process 300 may set intensity values of the pixels based on intensity values of each coverage area at the pixel location of a given pixel. The process 300 can set the intensity value at pixel locations near bordering coverage areas of the preliminary synthetic image as follows:

$$iv_p = w_1 iv_j + w_2 iv_k \qquad (1)$$

where $iv_p$ is the intensity value at a given pixel location of the preliminary synthetic image, $w_1$ and $w_2$ are a first weight and a second weight respectively that sum to one, and $iv_j$ and $iv_k$ are intensity values at the given pixel location for a first coverage area and a second coverage area respectively. In other words, $iv_j$ and $iv_k$ are the intensity values of the corresponding 2D slice at the given pixel location. For pixels located at the border between coverage areas, for example where each pixel is only one step away in an x-direction or y-direction, the first weight $w_1$ and the second weight $w_2$ can each be set to 0.5, reflecting an equal emphasis on the "home" coverage area (i.e., the coverage area that the pixel is located within) and the coverage area bordering the home coverage area. For pixels located further away from the border, such as a pixel located two pixels away from the border within the first coverage area, the first weight $w_1$ can be set equal to 0.8 and the second weight $w_2$ can be set equal to 0.2, reflecting a greater emphasis on the home coverage area of the pixel. In some embodiments, the process 300 can set the weights using a mathematical function, such as a linearly increasing/decreasing function. For example, for a pixel located on the border, a pixel located one pixel away from the border, and a pixel located two pixels away from the border, the process 300 can set the first weight $w_1$ to be 0.5, 0.75, and 1.0 respectively, and the second weight $w_2$ to be 0.5, 0.25, and 0.0 respectively. The weights may be set using another mathematical function, such as logarithmically increasing/decreasing or exponentially increasing/decreasing the weights away from the border, as long as the weights sum to one. The process 300 may only determine the intensity value of pixels using equation (1) above if the pixels are located within a threshold distance of a border between neighboring coverage regions, such as less than three pixels away from the border. The process 300 can then determine the intensity value of any pixels within the threshold distance using equation (1) and an applicable mathematical function, such as a linearly increasing/decreasing function. Pixels that are not within the threshold distance may retain the intensity values assigned earlier. After edges of the coverage areas have been blended, the process 300 can set the final synthetic image equal to the (processed) preliminary synthetic image. The process 300 can then proceed to 344.

At 344, the process 300 can output the final synthetic image to a memory for storage and/or use by another process, and/or to a display such as a computer monitor for viewing by a human practitioner. For example, the process 300 can output the final synthetic image to a display in a medical facility to allow a medical practitioner to view the final synthetic image and potentially infer information about tumors and/or lesions present in the final synthetic image. As another example, an additional process (that will be described below) may utilize the final synthetic image to predict a likelihood of malignancy of tumors and/or lesions in breast tissue. The final synthetic image may be used to replace the storage of all the slices included in the 3D tomosynthesis data, which can save memory space as only the array of pixels of the final synthetic data and data about the associated regions of interest may need to be stored instead of 10-150 slices or more. This reduction in memory requirements can reduce the size of servers required by an information technology system used by a hospital. The process 300 can then proceed to 348.

At 348, the process can determine whether or not additional synthetic 2D images should be generated. The process 300 may determine if the number of ROIs contains at least one ROI. If the number of ROIs does not contain at least one ROI, the process 300 can determine that no more synthetic images should be generated. If the number of ROIs does contain at least one ROI, the process 300 can determine that more synthetic images should be generated. The process can then proceed to 352.

At 352, if the process 300 determined that no more synthetic images should be generated, the process 300 can proceed to end. If the process 300 determined that more synthetic images should be generated, the process 300 can proceed to 332.

Figure 4:
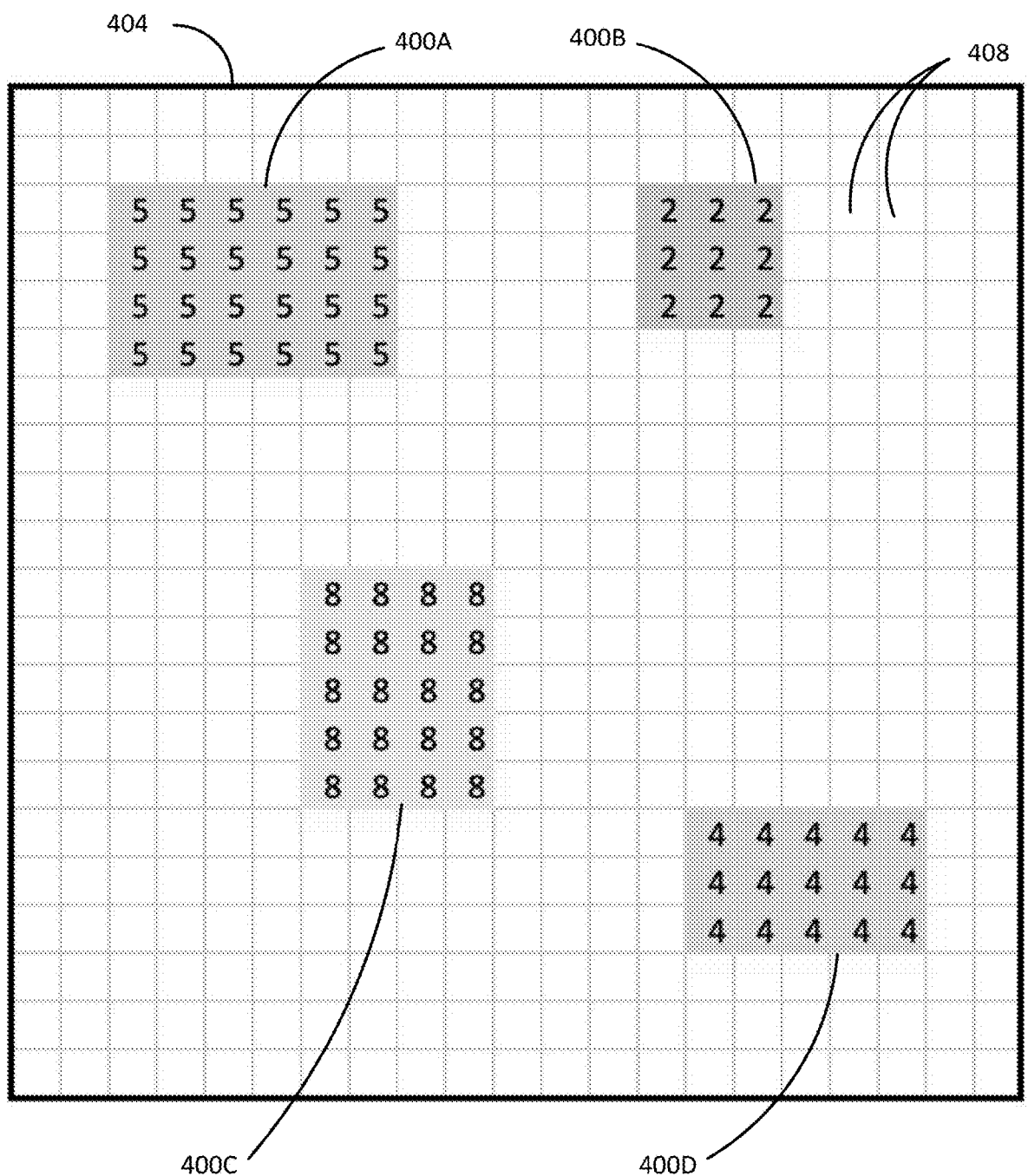
FIG. 4 is a schematic diagram that shows regions of interest associated with an exemplary preliminary synthetic image.

Referring to FIG. 3 as well as FIG. 4, ROIs associated with an exemplary preliminary synthetic image are shown. ROIs are shown arranged on an array 404 of the preliminary synthetic image. A first ROI 400A can be associated with a fifth 2D slice included in a set of 2D slices. A second ROI 400B can be associated with a second 2D slice included in the set of 2D slices. A third ROI 400C can be associated with an eighth 2D slice included in the set of 2D slices. A fourth ROI 400D can be associated with a fourth 2D slice included in the set of 2D slices. The array 404 can contain one or more unpopulated pixels 408. FIG. 4 can represent the state of the preliminary synthetic image after step 332 has been executed.

Figure 5:
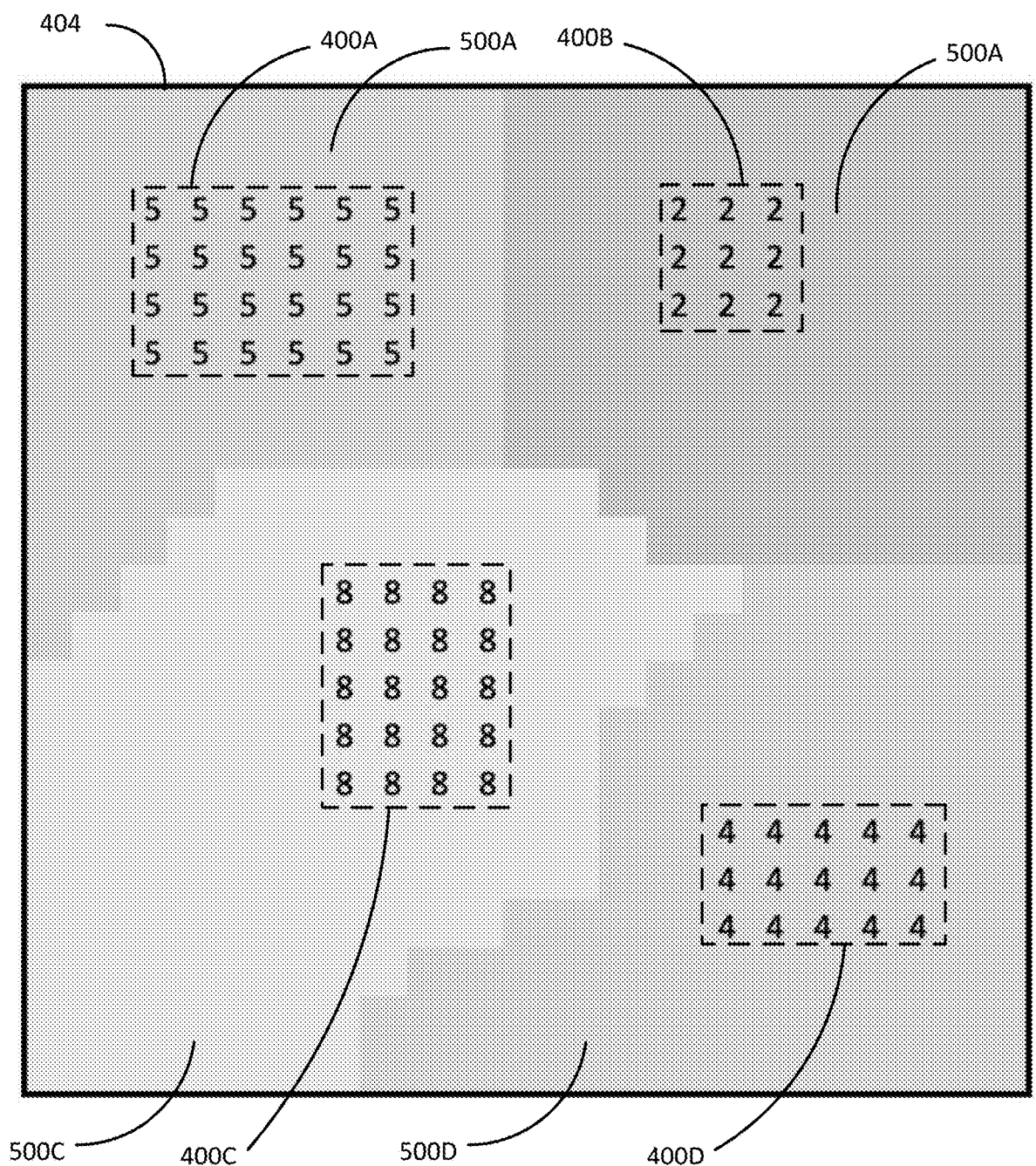
FIG. 5 is another schematic diagram that shows regions of interest and coverage areas associated with the exemplary preliminary synthetic image of FIG. 4.

Referring to FIGS. 3 and 4 as well as FIG. 5, ROIs and coverage areas associated with the exemplary preliminary synthetic image of FIG. 4 are shown. The first ROI 400A can be associated with a first coverage area 500A. The second ROI 400B can be associated with a second coverage area 500B. The third ROI 400C can be associated with a third coverage area 500C. The fourth ROI 400D can be associated with a fourth coverage area 500D. Each pixel of the array 404 can be associated with one of the coverage areas 500A-D. FIG. 5 can represent the state of the preliminary image after step 336 has been executed, in particular, after a watershed-by-flooding algorithm has been executed.

Figure 6:
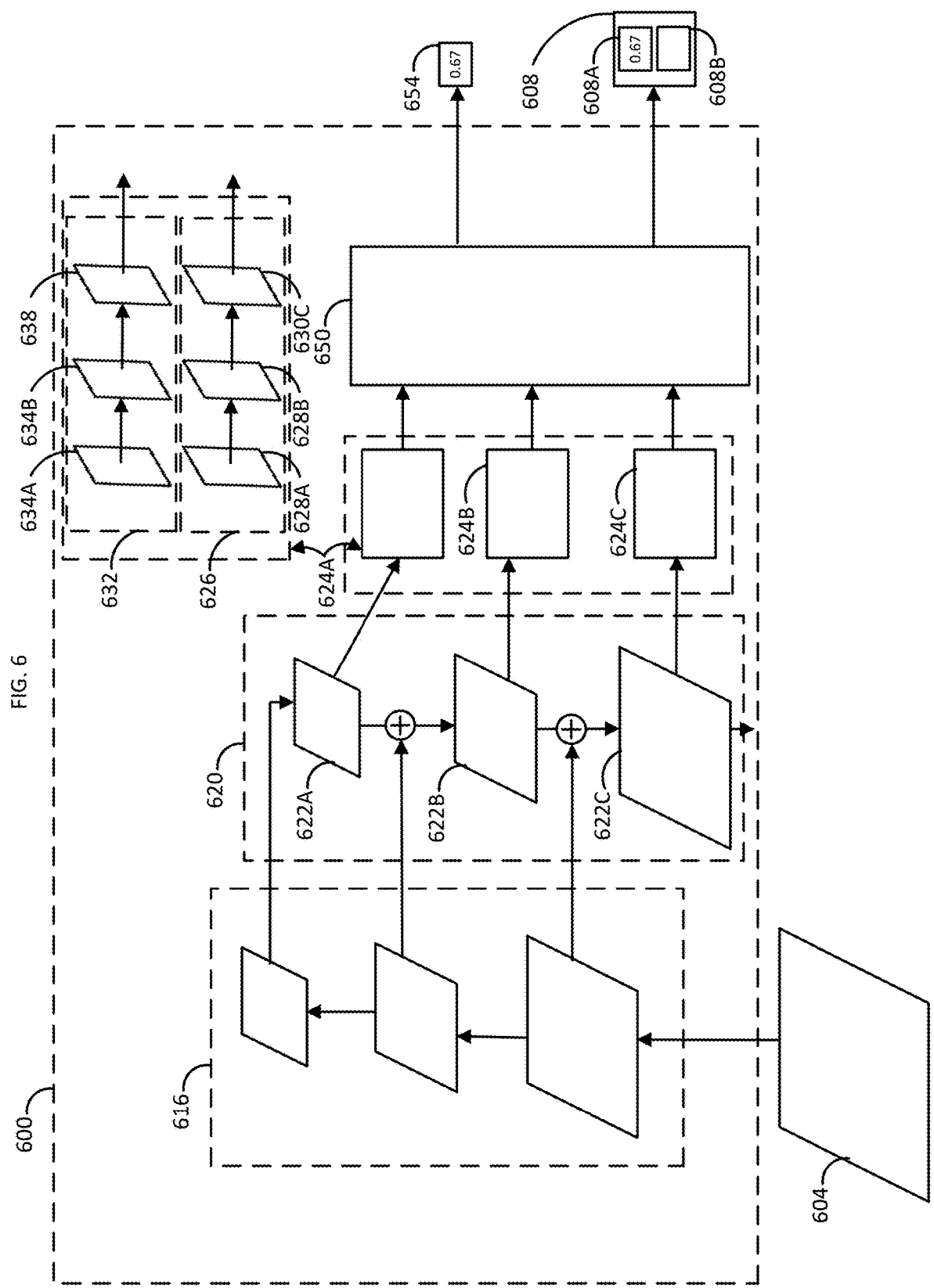
FIG. 6 is a further block diagram that shows an exemplary secondary model for generating a malignancy likelihood score.

Referring to FIG. 3 as well as FIG. 6, an exemplary secondary model 600 for generating a malignancy likelihood score 654 is shown. The secondary model 600 can receive an input synthetic image 604 that may be generated using the process 300 as described above and output the malignancy likelihood score 654 that can range from zero to one. In some embodiments, the malignancy likelihood score 654 can indicate a category of risk, i.e. a low risk, medium risk, or high risk category. In some embodiments, the malignancy likelihood score 654 can be selected from a range of values, such as the integers 1-5, with 1 indicating a lowest risk level and 5 indicating a highest risk level.

In some embodiments, the secondary model 600 can include a neural network such as a residual convolutional neural network. In order to train the secondary model 600, a training dataset including synthetic images labeled as malignant or non-malignant can be used to train the model. Human practitioners can label the synthetic images. For instance, a synthetic image corresponding to a patient known to have cancer could be given a label of "1", whereas a synthetic image corresponding to a patient known to not have cancer could be given a label of "0". In some embodiments, the synthetic images can be 300. Once trained, the secondary model 600 can receive an input synthetic image and output a malignancy likelihood score indicating whether or not the breast tissue contains malignant tumors and/or lesions.

The secondary model 600 can include a number of layers such as convolutional layers. It is understood that some embodiments of the secondary model 600 may have different numbers of layers, a different arrangement of layers or other differences. However, in all embodiments, the secondary model 600 can be capable of receiving an input 2D synthetic image and outputting a malignancy likelihood score. The secondary model 600 can be a one-stage detection network including one or more subnetworks.

Briefly referring back to FIG. 2 as well as FIG. 6, the secondary model 600 can include a primary subnetwork 616 and a secondary subnetwork 620, which can be the same as the primary subnetwork 216 and the secondary subnetwork 220 of the model 200 described above. In some embodiments, the primary subnetwork 616 and the secondary subnetwork 620 can be the same as the primary subnetwork 216 and the secondary subnetwork 220 after the model 200 has been trained. In other words, the secondary model 600 can be initialized with weights from the model 200 before training.

The secondary model 600 is important because the model 200 described above may be able to detect regions of the breast tissue that are of interest, but may not be able to accurately determine if the ROIs are actually malignant. The secondary model 600 may be used to more accurately estimate malignancy of the breast tissue using the synthetic images generated by the model 200 described above. In testing, the exemplary model 600 was observed to have a 0.03 increase in the area-under-the-curve (AUC) for a receiver operating characteristic (ROC) plot when tested on a set of 1000 unseen mammograms (100 cancers) using a synthetic image created using the process 300 as opposed to a synthetic image created using an imaging equipment manufacturers default image generation technique.

The model 600 can include a plurality of tertiary subnetworks, such as a first tertiary network 624A, a second tertiary network 624B, and a third tertiary network 624C. Each of the tertiary networks 624A-C can be connected to a layer of the second subnetwork 620. The first tertiary network 624A can be connected to a first layer 622A, the second tertiary network 624B can be connected to a second layer 622B, and the third tertiary network 624C can be connected to a third layer 622C. Each tertiary network can receive features from a layer of the second subnetwork 620 in order to estimate malignancy of the breast tissue at different levels of scale.

Each tertiary network can include a box regression subnetwork 626. The box regression subnetwork 626 can include one or more convolutional layers 628A-B, each followed by rectified linear (ReLU) activations, and a final convolutional layer 630 configured to output regression coordinates corresponding to anchors associated with a portion of one of the layers of the second subnetwork 620 (and corresponding to an array of pixels of the input synthetic 2D slice 604). The anchors can be predetermined subarrays of the various layers of the second subnetwork 620. The regression coordinates can represent a predicted offset between an anchor and a predicted bounding box. For each bounding box included in an ROI, a set of regression coordinates (e.g. four regression coordinates) and the corresponding anchor can be used to calculate the coordinates of the bounding box.

Each tertiary network can include a classification subnetwork 632. The classification subnetwork 632 can include one or more convolutional layers 634A-B, each followed by ReLU activations, and a final convolutional layer 638 followed by sigmoidal activations to output predictions of object presence (i.e., malignant tumor and/or lesion presence). The classification subnetwork 632 can be used to obtain one or more estimations of whether or not a patient has a malignant tumor and/or lesion at various spatial locations of the synthetic 2D slice 604. More specifically, each bounding box can be associated with an estimated score output by the classification subnetwork 632. The bounding box can also be associated with a slice number as described above. In some embodiments, the value of each estimated score can range from zero to one. One of the spatial locations can include an entire layer, i.e., first layer 622A, of the second subnetwork 620. In this way, the classification subnetwork 632 can output an estimation of whether or not a patient has a malignant tumor and/or lesion based on a 2D slice. It is contemplated that the final convolutional layer 638 can be followed by Softmax activations in models that are trained to classify multiple types of malignant regions, for example multiple levels of malignancy (e.g., low risk regions, high risk regions, etc.).

The model 600 can include an output layer 650 for normalizing data across different scales, calculating bounding box coordinates, and filtering out low scoring bounding box predictions. The output layer 650 can receive outputs from the tertiary subnetworks 624A-C and output one or more ROIs, each ROI including an array of pixels scaled to the array size of the 2D slice 604 and an associated score. The array of pixels can be a bounding box (e.g., a rectangular bounding box) calculated based on the regression coordinates and the anchors. The output layer 650 can filter out any scores below a predetermined threshold, for example, 0.5. After filtering, the output layer 650 can determine the array of pixels of each ROI based on the one or more anchors associated with the remaining scores. The output layer 650 may resize the anchors in order to match the scale of the 2D slice 604, as may be necessary for anchors associated with smaller layers of the second subnetwork 620, before including the anchor as the array of an output ROI. The output layer 650 can receive outputs from the tertiary subnetworks 624A-C and output the malignancy likelihood score 654. In some embodiments, the malignancy likelihood score 654 can be selected to be the highest scoring bounding box score. In some embodiments, the model 600 can output one or more ROIs 608, each including a score 608A and an array of pixels 608B. The array of pixels 208B can be a rectangular bounding box. The one or more ROIs 608 can provide additional information to a practitioner about potentially malignant regions of the synthetic image 604.

Figure 7:
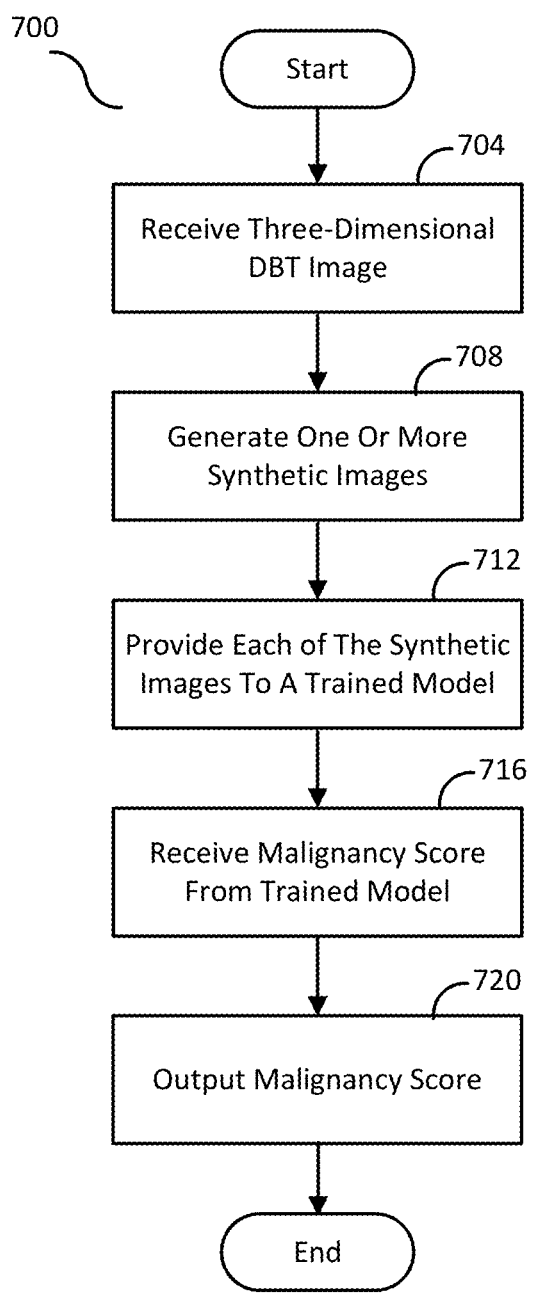
FIG. 7 is a flow chart that shows some example of steps in a process for creating a synthetic image using a model trained to estimate malignancy of tumors and/or lesion in breast tissue.

Referring now to FIGS. 1, 3, and 6 as well as FIG. 7, a process 700 for creating a synthetic image using a model trained to estimate malignancy of tumors and/or lesion in breast tissue and generating a malignancy likelihood score based on the synthetic image is shown. The process 700 can be implemented as instructions on one or more memories included in a data processing system. The data processing system can further include one or more processors in communication with the one or more memories and configured to execute the instructions. The one or more processors can be configured to access a memory, which can be included in the mass storage device 128, having 3D tomosynthesis data including a number of two-dimensional slices stored thereon.

At 704, the process 700 can receive 3D tomosynthesis data of breast tissue of a patient. The 3D tomosynthesis data can be generated by a 3D mammography imaging system such the x-ray imaging system 100. The 3D tomosynthesis data can include a number of 2D slices corresponding to a predetermined thickness, such as 1 mm, of the breast tissue. Depending on the patient and/or imaging system, the 3D tomosynthesis data may include about 10-150 or more 2D slices. Each 2D slice can be an array of pixels of a predetermined size, such as 2000×1500 pixels. The process 700 can then proceed to 708.

At 708, the process 700 can generate one or more synthetic images (i.e., mammograms) using at least one of steps 308-352 described above. The process 700 can then proceed to 712.

At 712, the process 700 can provide each of the one or more synthetic images to a trained model for determining a malignancy likelihood score. The trained model can be model 600 as described above. The process 700 can then proceed to 716.

At 716, the process 700 can receive a malignancy likelihood score from the trained model. In some embodiments, the malignancy likelihood score can range from zero to one, inclusive, with one indicating a high risk of malignancy and zero indicating minimal or no risk of malignancy. In some embodiments, the malignancy can be a "yes" (i.e. 1) or "no" (i.e. 0), indicating if the tumor is predicted to be malignant or not malignant, respectively. In some embodiments, the malignancy likelihood score can indicate a category of risk, for example, a low risk, medium risk, or high risk category. In some embodiments, the malignancy likelihood score can be selected from a range of values, such as the integers 1-5, with 1 indicating a lowest risk level and 5 indicating a highest risk level. In some embodiments, the process 700 can also receive one or more regions of interest generated by the trained model such as the regions of interest 608 described above. The process 700 can then proceed to 720.

At 720, the process 700 can output the malignancy likelihood score to a memory for storage and/or use by another process, and/or to a display such as a computer monitor for viewing by a human practitioner. For example, the process 300 can output the malignancy likelihood score to a display in a medical facility to allow a medical practitioner to view the malignancy likelihood score and potentially determine a diagnosis of a patient based on the malignancy likelihood score. The malignancy likelihood score may be stored in a database of medical records for future analysis and/or studies of breast cancer patients. In some embodiments, the process 700 can also output one or more of the regions of interest received at 716 for storage and/or use by another process, and/or to a display such as a computer monitor for viewing by a human practitioner. The process 700 may output the malignancy likelihood score and/or the one or more regions of interest as a report. The process 700 can then end.

In testing, the processes 300 and 700 were shown to detect breast cancer presence in both dense and non-dense breasts. A first model in accordance with the model 200 in FIG. 2 was trained using an annotated FFDM dataset. A second model in accordance with the model 600 in FIG. 6 was trained using an annotated three-dimensional breast image dataset. To train the second model, slices included in three-dimensional images in the dataset were used to generate synthetic images using a process in accordance with the process 300 in FIG. 3. The synthetic images were then annotated by medical practitioners and provided to the second model for training. Each synthetic image can be annotated as having or not having cancer at a whole-image level. In some embodiments, each synthetic image can be annotated based on annotations associated with the annotated three-dimensional breast image dataset. Thus, the synthetic images can be weakly annotated. The first model and the second model were then tested using an additional three-dimensional breast image dataset using a process in accordance with the process 700 in FIG. 7. The second model was able to identify cancer in non-dense breasts (BIRADS A, B) at an area under the curve (AUC) of a receiver operating characteristic (ROC) curve of 0.96 with sensitivity of 92% at 88.9% specificity. The specificity was chosen based on the national average. Additionally, the second model was able to identify cancer in dense breasts (BIRADS C, D) at an AUC of a ROC curve of 0.94 with sensitivity of 85% at 88.9% specificity. Overall, performance on the additional three-dimensional breast image dataset was an AUC of 0.95 and sensitivity of 91% at 88.9% specificity.

Figure 8:
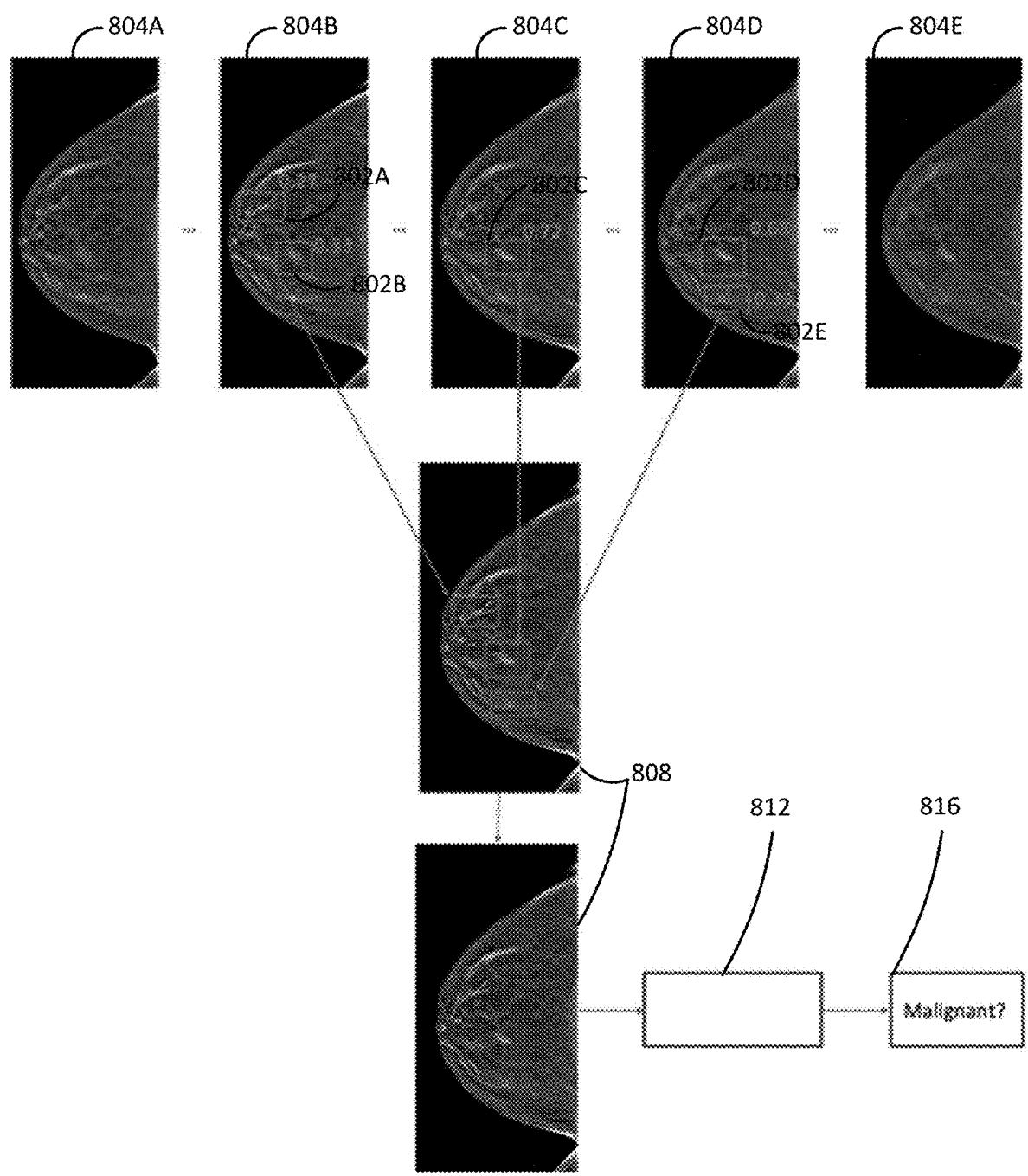
FIG. 8 is a collection of images that shows a visual dataflow path of the process of FIG. 7.

Referring now to FIG. 7 as well as FIG. 8, a visual dataflow path of the process 700 is shown. Generally, the process 700 determines ROIs 802A-E of various slices 804A-E of 3D DBT data using a trained model. A synthetic image 808 is then synthesized using a portion of the ROIs including ROI 802A, ROI 802C, and ROI 802E. The synthesized image 808 is then provided to a second trained model 812. The second trained model 812 then outputs a malignancy likelihood score 816.

Figure 9:
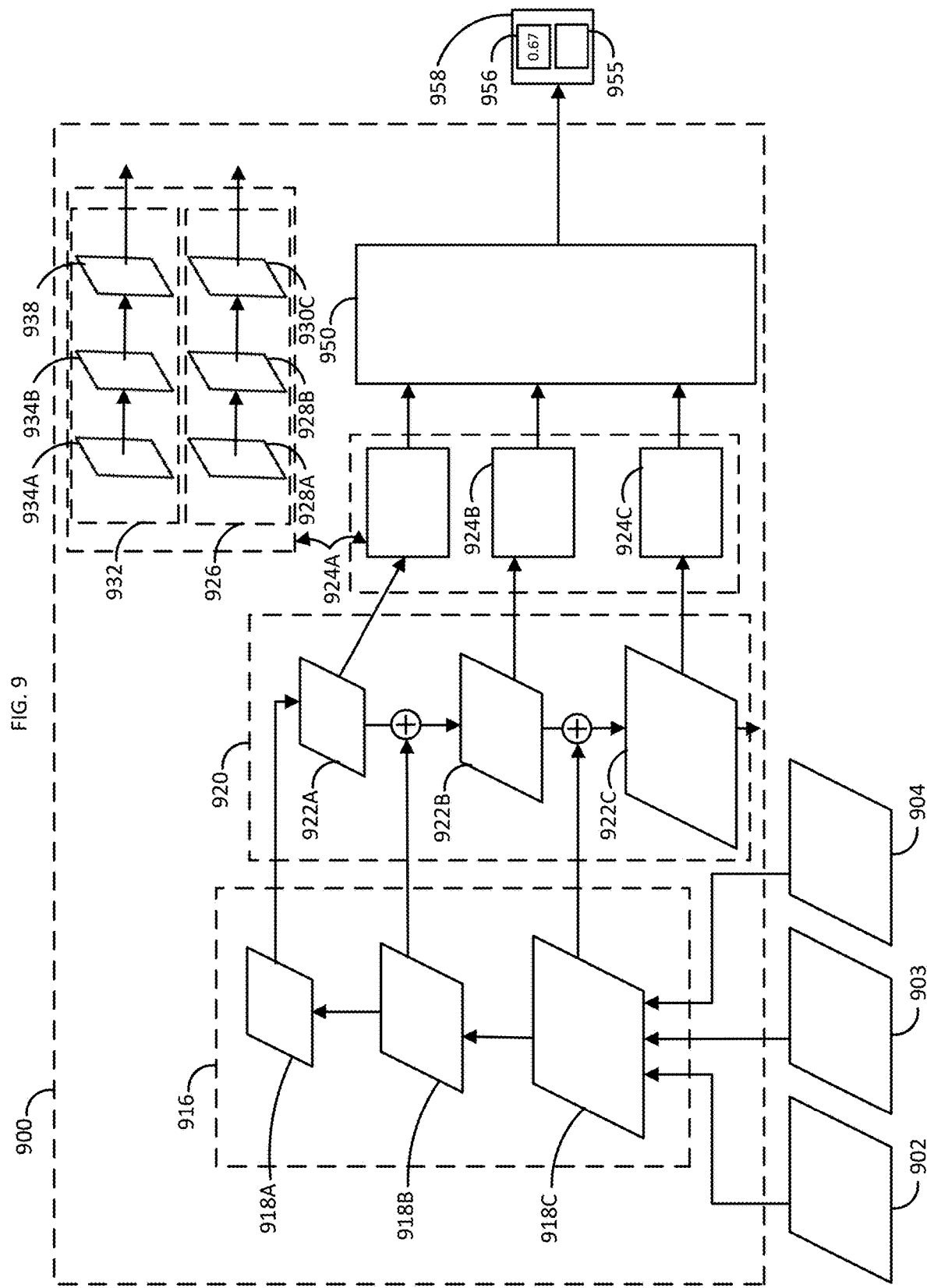
FIG. 9 is an exemplary embodiment of a model for generating regions of interest (ROIs) for a second 2D slice of 3D tomosynthesis data based on a first 2D slice of 3D tomosynthesis data, the second 2D slice of 3D tomosynthesis data, and a third 2D slice of 3D tomosynthesis data.

Referring to FIG. 9, an exemplary embodiment of a model 900 for generating regions of interest (ROIs) for a second 2D slice 903 of 3D tomosynthesis data based on a first 2D slice 902 of 3D tomosynthesis data, the second 2D slice 903 of 3D tomosynthesis data, and a third 2D slice 904 of 3D tomosynthesis data is shown. As will be described below, each of the first 2D slice 902, the second 2D slice 903, and the third 2D slice 904 can be provided to the model 900, and the model 900 can determine ROIs corresponding to the second 2D slice 903 based on the first 2D slice 902, the second 2D slice 903, and the third 2D slice 904. The model 900 can have three input channels for receiving three 2D slices. Each 2D slice and any ROIs associated with each 2D slice can be associated with an input channel of data that is analyzed by the model 900. For example, the first 2D slice 902 can be associated with a first input channel, the second 2D slice 903 can be associated with a second input channel, and the third 2D slice 904 can be associated with a third input channel. As will be explained further below, a synthetic image associated with the second input channel can be generated using one or more ROIs associated with the second input channel.

The ROIs may be referred to as indicators. The model 900 can accept the input 2D slices 902, 903, 904 and output any number of ROIs for the second 2D slice 903. Each ROI can be associated the second input 2D slice 903. For example, the model can output a first ROI 958 associated with the second 2D slice 903. Additionally, each ROI can be associated with a slice number indicating the 2D slice that was input to the second channel. For example, the second slice 903 may be the fourth slice of a set of seventy-five 2D slices, and the first ROI 958 can be associated with a slice number of four (e.g. fourth slice). The slice number can be used when selecting and/or combining ROIs to create a synthetic image, as will be explained below. As described above, each ROI can include an area and a score. For example, the first ROI 958 can include an area 955 and a score 956.

The slice numbers associated with the first 2D slice 902, the second 2D slice 903, and the third 2D slice 904 can be a predetermined value n apart. For example, if the second 2D slice 903 is associated with a slice number $x_2$, the first 2D slice 902 can be associated with a slice number $x_1=x_2-n$ and the second 2D slice 904 can be associated with a slice number $x_3=x_2+n$, where n can range from one to five or more. In some embodiments, the predetermined value n can be three. When analyzing slice 903, the slices 902 and 904 can provide volumetric context to the model 900 that may be helpful in predicting whether malignant tumors and/or lesions are present in the breast tissue represented by slice 903.

Each of the first 2D slice 902, the second 2D slice 903, and the third 2D slice 904 can be formatted as an array of pixels of a predetermined size, for example 2000×1500. The pixels can include a single intensity value (e.g., a white intensity value). The pixels of the ROI can include a single intensity values (e.g., a white intensity value) and a location within the associated 2D slice (e.g., the pixel at a given (x, y) location in a 2000×1500 pixel slice).

In addition to the subarray of pixels, each ROI can include a relevancy score indicating how relevant the subarray of pixels is in determining a malignancy likelihood score (which will be explained below in conjunction with FIG. 11). The relevancy score can be used to create a synthetic 2D image using one or more ROIs, as will be explained in detail below. The relevancy score can be selected from a range of values such as between 0 and 1. When identifying ROIs for a training dataset, a human practitioner can assign relevancy scores for each ROI within the range of the values. The human practitioner could alternatively assign relevancy scores using a different scale, such as 0-100 (with higher scores indication higher potential for malignancy) which could then be normalized to relevancy score range used by the model 900. In some embodiments, the human practitioner can identify ROIs as benign in order to better train the model 900 to identify potentially malignant ROIs.

In some embodiments, the model 900 can include a neural network such as a convolutional neural network. In order to train the model 900, a training dataset consisting of slices from a set of 3D tomosynthesis images and pre-identified (e.g., by one or more medical practitioners) ROIs can be used to train the model. During the training of model 900 on 3D tomosynthesis images, 2D full-field digital mammography (FFDM) images, with respective ROIs, may also be included, in which case the 2D image can be replicated across all three input channels. For either the FFDM images or tomosynthesis slices, human practitioners can identify ROIs by examining a given 2D slice, outlining, using a predetermined shape such as a rectangular box, any regions that may be of interest, and assign a relevancy score to the predetermined shape based on their medical expertise and/or experience in evaluating tumors and/or lesions. Alternatively, the relevancy score can be assigned based on pathology results that indicate whether or not a lesion is malignant. A large training database can be generated by having one or more medical practitioners identify ROIs in 2D images taken from a plurality of FFDM images or slices of 3D tomosynthesis images (e.g., images of multiple patients). The model 900 can be trained by sequentially providing three slices offset at a predetermined offset value (e.g. n=1) for tomosynthesis slices, or by replicating a given FFDM image across the three input channels, and including any associated ROIs in either case. Once trained, the model 900 can receive three input 2D slices and output one or more ROIs, each ROI including an estimated relevancy score and a subarray of pixels of the second 2D slice 903.

The model 900 can include a number of layers such as convolutional layers. It is understood that some embodiments of the model 900 may have different numbers of layers, a different arrangement of layers or other differences. However, in all embodiments, the model 900 can be capable of receiving three 2D input slices and outputting any regions of interest associated with the second 2D slice 903. The model 900 can be a one-stage detection network including one or more subnetworks.

The model 900 can include a first subnetwork 916. The first subnetwork 916 can be a feedforward residual neural network ("ResNet") with one or more layers 918A-C. The layer 918C can be an input layer configured to accept the three input 2D slices 902, 903, and 904. In this way, the model 900 can detect potential ROIs in a specific slice, such as the first 2D slice 902, using data from all three slices 902, 903, and 904. A second subnetwork 920 can be built on top of the first subnetwork to effectively create a single neural network, using the first subnetwork 916 as the backbone for the network. The second subnetwork 920 can contain a plurality of layers including a first layer 922A, a second layer 922B, and a third layer 922C, though other numbers of layers (i.e., five layers) can be used, and three layers are shown for simplicity. Each of the first layer 922A, the second layer 922B, and the third layer 922C can be a convolutional layer. Each layer can be made of a number of building blocks (not shown). Each building block can include a number of parameters layers such as three parameter layers, each parameter layer including a number of filters (e.g., 256) with a given filter size (e.g., 3×3). Each of the first layer 922A, the second layer 922B, and the third layer 922C can have an associated output size such as 144×144, 72×72, and 36×36 for each input 2D slice. The output sizes can vary between input slices based on pre-processing conditions and/or parameters. As the output size decreases between layers of the second subnetwork 920, the number of filters of the parameter layers can increase proportionally, i.e., halving output size results in doubling the number of filters. The second subnetwork can also include a global average pooling layer connected to a final layer (i.e., the third layer 922C), a fully-connected layer connected to the global average pooling layer, and a softmax layer connected to the fully-connected layer and having a 1×1 output size (i.e., a single value).

The model 900 can include a plurality of tertiary subnetworks such as a first tertiary network 924A, a second tertiary network 924B, and a third tertiary network 924C. Each of the tertiary networks 924A-C can be connected to a layer of the second subnetwork 920. The first tertiary network 924A can be connected to the first layer 922A, the second tertiary network 924B can be connected to the second layer 922B, and the third tertiary network 924C can be connected to the third layer 922C. Each tertiary network can receive features from a layer of the second subnetwork 920 in order to detect tumors and/or lesions at different levels of scale in each of the input 2D slices 902, 903, and 904.

Each tertiary network can include a box regression subnetwork 926. The box regression subnetwork 926 can include one or more convolutional layers 928A-B, each followed by rectified linear (ReLU) activations, and a final convolutional layer 930 configured to output regression coordinates corresponding to anchors associated with a portion of one of the layers of the second subnetwork 920 (and corresponding to an array of pixels of the second input 2D slice 903). The anchors can be predetermined subarrays of the various layers of the second subnetwork 920. The regression coordinates can represent a predicted offset between an anchor and a predicted bounding box. For each bounding box included in an ROI, a set of regression coordinates (e.g. four regression coordinates) and the corresponding anchor can be used to calculate the coordinates of the bounding box.

Each tertiary network can include a classification subnetwork 932. The classification subnetwork 932 can include one or more convolutional layers 934A-B, each followed by ReLU activations, and a final convolutional layer 938 followed by sigmoidal activations to output predictions of object presence (i.e., malignant tumor and/or lesion presence). The classification subnetwork 932 can be used to obtain one or more estimations of whether or not a patient has a malignant tumor and/or lesion at various spatial locations of the second input 2D slice 903. More specifically, each bounding box can be associated with an estimated score output by the classification subnetwork. In some embodiments, the value of each estimated score can range from zero to one. It is contemplated that the final convolutional layer 938 can be followed by Softmax activations in models that are trained to classify multiple types of malignant regions, for example multiple levels of malignancy (e.g., low risk regions, high risk regions, etc.).

The model 900 can include an output layer 950 for normalizing data across different scales, calculating bounding box coordinates, and filtering out low scoring bounding box predictions. The output layer 950 can receive outputs from the tertiary subnetworks 924A-C and output one or more ROIs, each ROI including an array of pixels scaled to the array size of the input 2D slice 903 and an associated score. The array of pixels can be a bounding box (e.g., a rectangular bounding box) calculated based on the regression coordinates and the anchors. The output layer 950 can filter out any scores below a predetermined threshold, for example, 0.5. In some embodiments, the output layer 950 can receive outputs from the tertiary subnetworks 924A-C and output a single malignancy likelihood score. In some embodiments, the single malignancy likelihood score can be selected to be the highest scoring bounding box score associated with any of the input 2D 903.

Figure 10:
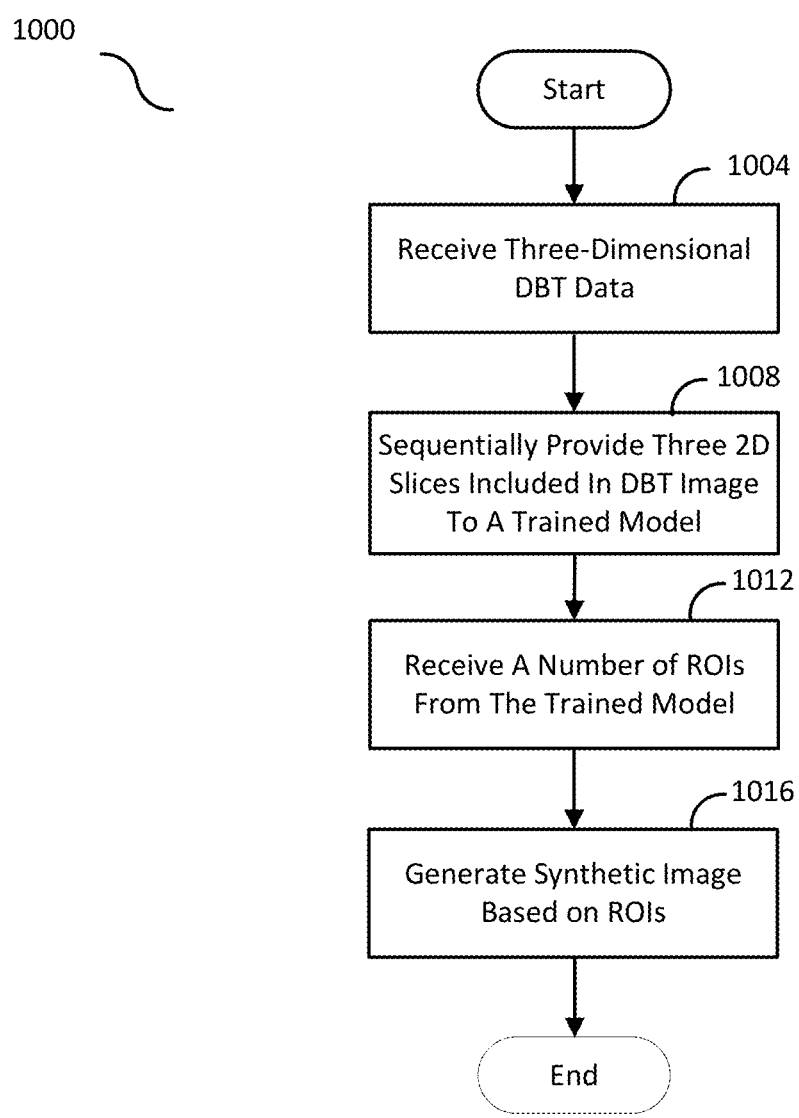
FIG. 10 is a process for generating synthetic images using the model of FIG. 9.

Referring now to FIGS. 1, 3, 6, 7, and 9 as well as FIG. 10, a process 1000 for generating synthetic images using the model 900 is shown. Generally, the process 1000 generates a synthetic image based on ROIs associated with the second input channel of the model 900. The ROIs can be generated using the model 900 described above. After the process 1000 has generated the synthetic image, the synthetic image can be used to determine a malignancy likelihood score using the process 700 in conjunction with the model 600 described above. The process 1000 can be implemented as instructions on one or more memories included in a data processing system. The data processing system can further include one or more processors in communication with the one or more memories and configured to execute the instructions. The one or more processors can be configured to access a memory, which can be included in the mass storage device 128, having 3D tomosynthesis data including a number of two-dimensional slices stored thereon.

At 1004, the process 1000 can receive 3D tomosynthesis data of breast tissue of a patient. The 3D tomosynthesis data can include a number of 2D slices corresponding to a predetermined thickness, such as 1 mm, of the breast tissue. Step 1004 may be the same as step 304 described above. The process 1000 can then proceed to 1008.

At 1008, the process 1000 can sequentially provide the 2D slices included in the 3D tomosynthesis data to a trained model. The trained model can be the model 900 trained as described above. The process 1000 can provide three 2D slices included in the 3D tomosynthesis data to the trained model for concurrent processing. In some embodiments, the trained model can be trained based on an image dataset including two-dimensional full-field digital mammography images annotated by a medical practitioner. Each of the three 2D slices is provided to a different input channel of the trained model. For example, a first 2D slice can be provided to a first input channel, a second 2D slice can be provided to a second input channel, and a third 2D slice can be provided to a third input channel. The 2D slices can have associated slice numbers that differ by a predetermined offset value. For example, if the offset value is two, the first 2D slice may be associated with a slice number of one, the second 2D slice may be associated with a slice number of three, and the third 2D slice may be associated with a slice number of five. In some embodiments, the process 1000 may provide three 2D slices to the process until all slices have been provided to the second input channel (along with the slices offset by the offset value being provided to the first and second channels). For some 2D slices, there may not be another 2D slice with a slice number the predetermined offset value less or more than the slice number of the 2D slice. For example, if the 2D slice provided to the second input channel has an associated slice number of one, and the offset value is two, the slice number of the 2D slice provided to the first input channel would be negative one. In such cases, the process 1000 can provide the next closest slice (e.g., the 2D slice associated with a slice number of one) to the first channel. The process can then "move up" through the 2D slices by increasing the slice numbers associated with the 2D slices to be provided by one. For example, the process 1000 can provide a 2D slices associated with slice numbers of one, three and five, and then provide 2D slices associated with slice numbers of two, four and six. In some embodiments, the process 1000 may provide a subset of the 2D slices to the second channel model 900, such as every other slice, every third slice, etc. Once every 2D slice (or every other slice, every third slice, etc.) has been provided to the trained model at least once, the process 1000 can proceed to 1012.

At 1012, the process 1000 can receive a number of ROIs from the trained model. Each ROI can be associated with the second input channel and one of the 2D slices. Each ROI can be generated when the associated 2D slice is provided to the trained model along with the 2D slices provided to the first channel and third channel of the trained model. The process 1000 can then proceed to 1016.

At 1016, the process 1000 can generate and output a synthetic image based on the number of ROIs. Using the number of ROIs generated at 1012, the process 1000 may execute at least a portion of steps 316-352 as described above. The process 1000 can then proceed to 1024. The process 1000 can then end.

Figure 11:
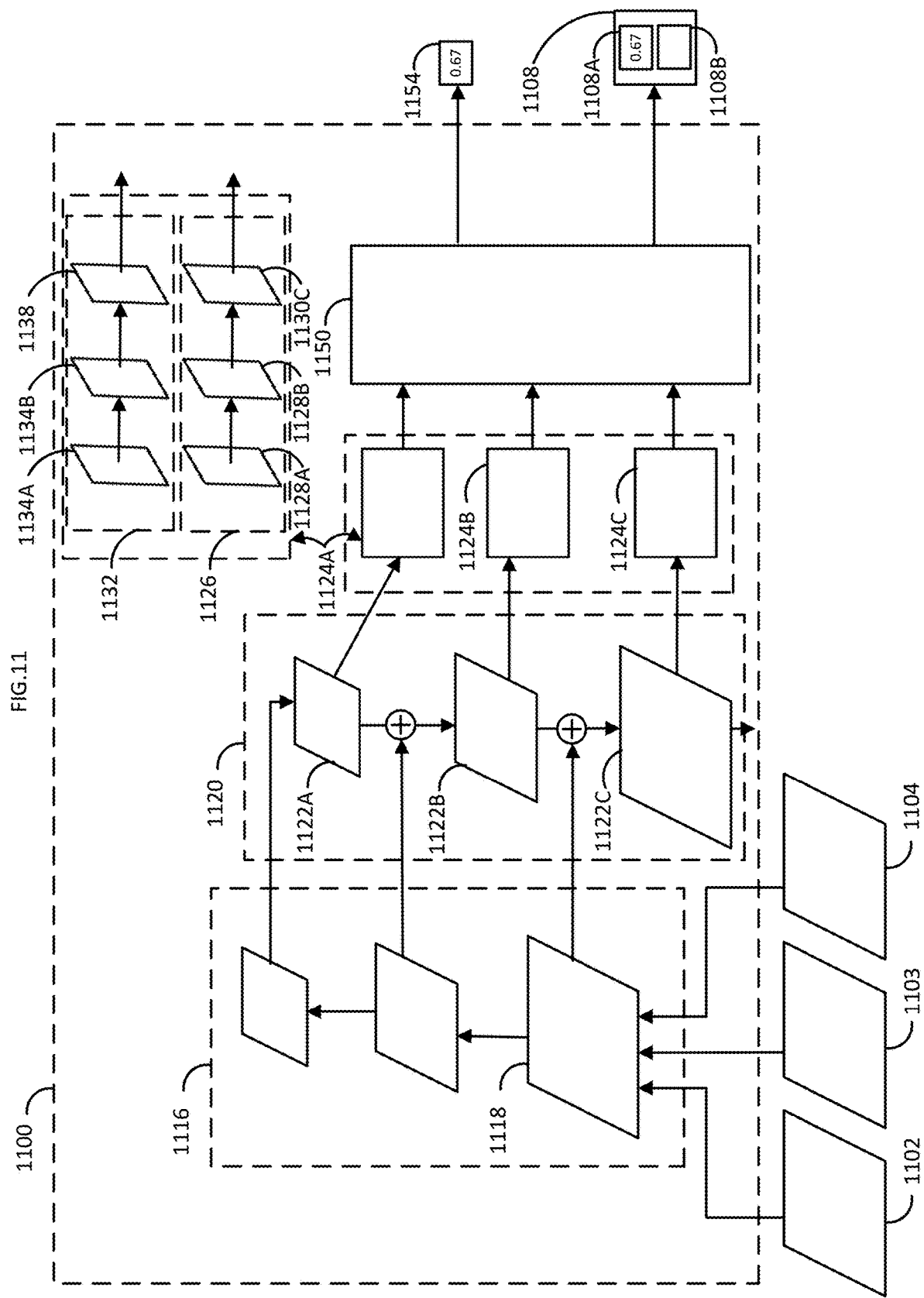
FIG. 11 is another exemplary secondary model for generating a malignancy likelihood score.

Referring to FIG. 10 as well as FIG. 11, an exemplary secondary model 1100 for generating a malignancy likelihood score 1154 is shown. The secondary model 1100 can receive three input synthetic images including a first synthetic image 1102, a second synthetic image 1103, and a third synthetic image 1104. The second synthetic image 1103 can be generated using the process 1000 as described above. The first and third synthetic images can be generated based on the second synthetic image and one or more 2D slices as will be described below. The model 1100 can output the malignancy likelihood score 1154 that can range from zero to one. In some embodiments, the malignancy likelihood score 1154 can indicate a category of risk, i.e. a low risk, medium risk, or high risk category. In some embodiments, the malignancy likelihood score 1154 can be selected from a range of values, such as the integers 1-5, with 1 indicating a lowest risk level and 5 indicating a highest risk level. The second synthetic image 1103 can be generated using the model 200 or the model 1000 described above.

As described above, each pixel included in the synthetic image can be associated with a slice number (or multiple slices if a blending technique is used, for example). For example, a first group of pixels included the second synthetic image 1103 can be associated with a seventh slice and a second group of pixels included in the synthetic image can be associated with a fifth slice. The intensity value of each pixel included in the first synthetic image 1102 and the third synthetic image 1104 can be determined by selecting intensity values from pixels included in slices plus or minus a predetermined offset number of slices away from the slice associated with a pixel at a given location in the second synthetic image 1103 (i.e., x−n for the first synthetic image 1102 and x+n for the third synthetic image 1104, where x is the slice number associated with a pixel included in the second synthetic image 1103 and n is the predetermined offset number of slices). For example, with a predetermined offset number of slices is one, the intensity values of pixels included in the first synthetic image 1102 at the same pixel locations as the first group of pixels (included in the second synthetic image 1103 and associated with the seventh slice) can be set equal to the intensity values of pixels included in the sixth slice and located at the same locations as the first group of pixels. For the third synthetic image 1104, the intensity values of pixels included in the third synthetic image 1104 at the same pixel locations as the first group of pixels (included in the second synthetic image 1103 and associated with the seventh slice) can be set equal to the intensity values of pixels included in the eighth slice and located at the same locations as the first group of pixels.

In embodiments where blending has been used to create the second synthetic image 1103, the intensity value of each pixel included in the first and third synthetic images 1102, 1104 can be set equal to the sum of each of the intensity values of pixels included in slices the predetermined offset number of slices away from the each slice used to generate the second synthetic image 1103 multiplied by the weights used to generate the second synthetic image 1103.

In some embodiments, the secondary model 1100 can include a neural network such as a residual convolutional neural network. In order to train the secondary model 1100, a training dataset including synthetic images labeled as malignant or non-malignant can be used to train the model. Human practitioners can label the synthetic images. Once trained, the secondary model 1100 can receive three input synthetic images generated from 3D tomosynthesis data of breast tissue and output a malignancy likelihood score indicating whether or not the breast tissue contains malignant tumors and/or lesions.

The secondary model 1100 can include a number of layers such as convolutional layers. It is understood that some embodiments of the secondary model 1100 may have different numbers of layers, a different arrangement of layers or other differences. However, in all embodiments, the secondary model 1100 can be capable of receiving three input 2D synthetic images and outputting a malignancy likelihood score. The secondary model 1100 can be a one-stage detection network including one or more subnetworks.

Briefly referring back to FIG. 9 as well as FIG. 11, the secondary model 1100 can include a primary subnetwork 1116 and a secondary subnetwork 1120, which can be the same as the primary subnetwork 916 and the secondary subnetwork 920 of the model 900 described above. In some embodiments, the primary subnetwork 1116 and a secondary subnetwork 1120 can be the same as the primary subnetwork 916 and a secondary subnetwork 920 after the model 900 has been trained. In other words, the secondary model 1100 can be initialized with weights from the model 900, the model 600, or the model 200 described above before training. The primary subnetwork 1116 can include an input layer 1118 configured to receive three input synthetic images.

The secondary model 1100 is important because the model 900 described above may be able to detect regions of the breast tissue that are of interest, but may not be able to accurately determine if the ROIs are actually malignant. The secondary model 1100 may be used to more accurately estimate malignancy of the breast tissue using the synthetic images generated by the model 900 described above.

The model 1100 can include a plurality of tertiary subnetworks, such as a first tertiary network 1124A, a second tertiary network 1124B, and a third tertiary network 1124C. Each of the tertiary networks 1124A-C can be connected to a layer of the second subnetwork 1120. The first tertiary network 1124A can be connected to a first layer 1122A, the second tertiary network 1124B can be connected to a second layer 1122B, and the third tertiary network 1124C can be connected to a third layer 1122C. Each tertiary network can receive features from a layer of the second subnetwork 1120 in order to estimate malignancy of the breast tissue at different levels of scale.

Each tertiary network can include a box regression subnetwork 1126. The box regression subnetwork 1126 can include one or more convolutional layers 1128A-B, each followed by rectified linear (ReLU) activations, and a final convolutional layer 1130 configured to output regression coordinates corresponding to anchors associated with a portion of one of the layers of the second subnetwork 1120 (and corresponding to an array of pixels included in the second input synthetic 2D slice 1103). The anchors can be predetermined subarrays of the various layers of the second subnetwork 1120. The regression coordinates can represent a predicted offset between an anchor and a predicted bounding box. For each bounding box included in an ROI, a set of regression coordinates (e.g. four regression coordinates) and the corresponding anchor can be used to calculate the coordinates of the bounding box.

Each tertiary network can include a classification subnetwork 1132. The classification subnetwork 1132 can include one or more convolutional layers 1134A-B, each followed by ReLU activations, and a final convolutional layer 1138 followed by sigmoidal activations to output predictions of object presence (i.e., malignant tumor and/or lesion presence). The classification subnetwork 1132 can be used to obtain one or more estimations of whether or not a patient has a malignant tumor and/or lesion at various spatial locations of the second input synthetic 2D slice 1103. More specifically, each bounding box can be associated with an estimated score output by the classification subnetwork 1132. The bounding box can also be associated with a slice number as described above. In some embodiments, the value of each estimated score can range from zero to one. One of the spatial locations can include an entire layer, i.e., first layer 1122A, of the second subnetwork 1120. In this way, the classification subnetwork 1132 can output an estimation of whether or not a patient has a malignant tumor and/or lesion based on a synthetic 2D slice. It is contemplated that the final convolutional layer 1138 can be followed by Softmax activations in models that are trained to classify multiple types of malignant regions, for example multiple levels of malignancy (e.g., low risk regions, high risk regions, etc.).

The model 1100 can include an output layer 1150 for normalizing data across different scales, calculating bounding box coordinates, and filtering out low scoring bounding box predictions. The output layer 1150 can receive outputs from the tertiary subnetworks 1124A-C and output one or more ROIs, each ROI including an array of pixels scaled to the array size of the second input synthetic 2D slice 1103 and an associated score. The array of pixels can be a bounding box (e.g., a rectangular bounding box) calculated based on the regression coordinates and the anchors. The output layer 1150 can filter out any scores below a predetermined threshold, for example, 0.5. After filtering, the output layer 1150 can determine the array of pixels of each ROI based on the one or more anchors associated with the remaining scores. The output layer 1150 may resize the anchors in order to match the scale of the input synthetic 2D slices 1102, 1103, and 1104, as may be necessary for anchors associated with smaller layers of the second subnetwork 1120, before including the anchor as the array of an output ROI. The output layer 1150 can receive outputs from the tertiary subnetworks 1124A-C and output the malignancy likelihood score 1154. In some embodiments, the malignancy likelihood score 1154 can be selected to be the highest scoring bounding box score. In some embodiments, the model 1100 can output one or more ROIs 1108, each including a score 1108A and an array of pixels 11086. The array of pixels 11086 can be a rectangular bounding box. The one or more ROIs 1108 can provide additional information to a practitioner about potentially malignant regions of the second input synthetic 2D slices 1103.

Figure 12:
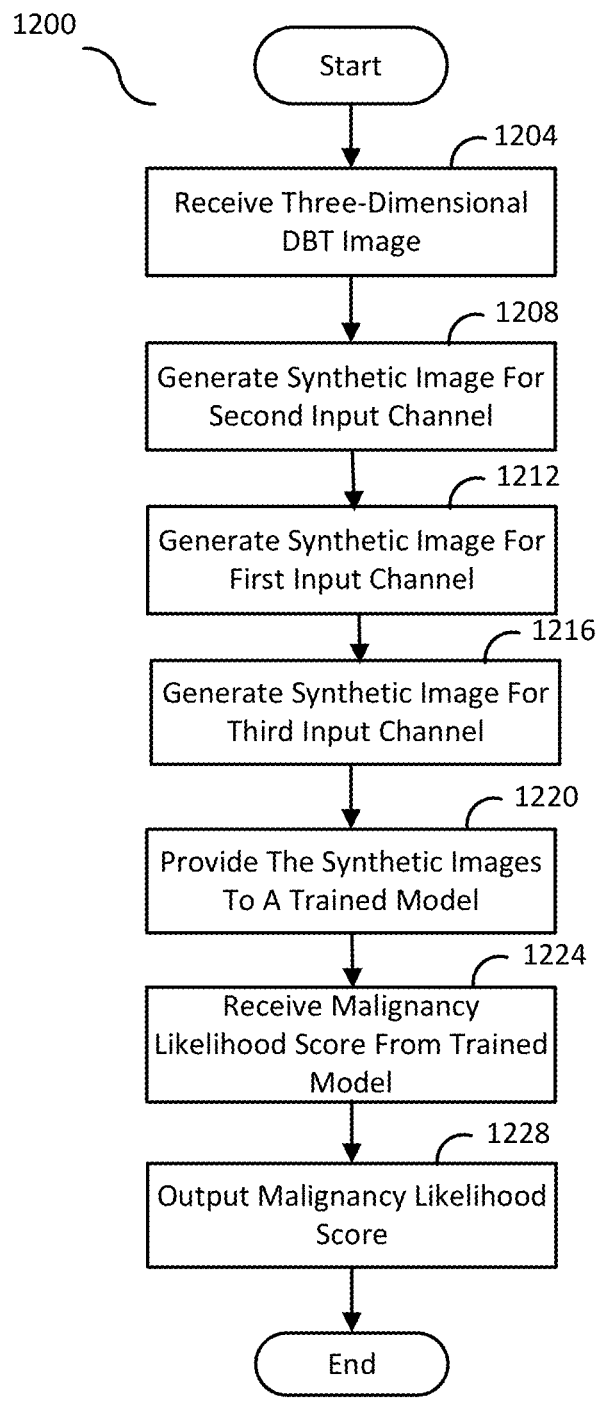
FIG. 12 is a process for creating three synthetic images using a model trained to estimate malignancy of tumors and/or lesion in breast tissue and generating a malignancy likelihood score based on the synthetic images.

Referring now to FIGS. 1, 9, and 11 as well as FIG. 12, a process 1200 for creating three synthetic images using a model trained to estimate malignancy of tumors and/or lesion in breast tissue and generating a malignancy likelihood score based on the synthetic images is shown. The process 1200 can be implemented as instructions on one or more memories included in a data processing system. The data processing system can further include one or more processors in communication with the one or more memories and configured to execute the instructions. The one or more processors can be configured to access a memory, which can be included in the mass storage device 128, having 3D tomosynthesis data including a number of two-dimensional slices stored thereon.

At 1204, the process 1200 can receive 3D tomosynthesis data of breast tissue of a patient. The 3D tomosynthesis data can be generated by a 3D mammography imaging system such as the x-ray imaging system 100. The 3D tomosynthesis data can include a number of 2D slices corresponding to a predetermined thickness, such as 1 mm, of the breast tissue. Depending on the patient and/or imaging system, the 3D tomosynthesis data may include about 10-150 or more 2D slices. Each 2D slice can be an array of pixels of a predetermined size, such as 2000×1500 pixels. The process 1200 can then proceed to 1208.

At 1208, the process 1200 can generate a synthetic image for the second input channel. The synthetic image is referred to as a second synthetic image (i.e., a synthetic image for the second channel of the model 1100), and can be generated using at least one of steps 1008-1016 described above. The process 1200 can then proceed to 1212.

At 1212, the process 1200 can generate a synthetic image for the first input channel, referred to as a first synthetic image (i.e., a synthetic image for the first channel of the model 1100), based on a predetermined offset number of slices and the second synthetic image. As described above, each pixel included in the synthetic image can be associated with a slice number (or multiple slices if a blending technique is used, for example). For example, a first group of pixels included the second synthetic image can be associated with a seventh slice and a second group of pixels included in the second synthetic image can be associated with a fifth slice. The process 1200 can determine the intensity value of each pixel included in the first synthetic image by selecting intensity values from pixels included in slices a predetermined offset number of slices below from the slice associated with a pixel at a given location in the second synthetic image (i.e., x−n for the first synthetic image, where x is the slice number associated with a pixel included in the second synthetic image and n is the predetermined offset number of slices). For example, with a predetermined offset number of slices is one, the intensity values of pixels included in the first synthetic image at the same pixel locations as the first group of pixels (included in the second synthetic image and associated with the seventh slice) can be set equal to the intensity values of pixels included in the sixth slice and located at the same locations as the first group of pixels. In embodiments where blending has been used to create the second synthetic image, the process 1200 can set the intensity value of each pixel included in the first synthetic image equal to the sum of each of the intensity values of pixels included in slices the predetermined offset number of slices away from the each slice used to generate the second synthetic image multiplied by the weights used to generate the second synthetic image. The process can then proceed to 1216.

At 1216, the process 1200 can generate a synthetic image for the third input channel, referred to as a third synthetic image (i.e., a synthetic image for the third channel of the model 1100), based on the predetermined offset number of slices and the second synthetic image. The process 1200 can determine the intensity value of each pixel included in the third synthetic image by selecting intensity values from pixels included in slices a predetermined offset number of slices above from the slice associated with a pixel at a given location in the second synthetic image (i.e., x+n for the third synthetic image, where x is the slice number associated with a pixel included in the second synthetic image and n is the predetermined offset number of slices). For example, with a predetermined offset number of slices is one, the intensity values of pixels included in the third synthetic image at the same pixel locations as the first group of pixels (included in the second synthetic image and associated with the seventh slice) can be set equal to the intensity values of pixels included in the eighth slice and located at the same locations as the first group of pixels. In embodiments where blending has been used to create the second synthetic image, the process 1200 can set the intensity value of each pixel included in the first and third synthetic images equal to the sum of each of the intensity values of pixels included in slices the predetermined offset number of slices away from the each slice used to generate the second synthetic image multiplied by the weights used to generate the second synthetic image. The process can then proceed to 1220.

At 1220, the process 1200 can provide the three synthetic images to a trained model for determining a malignancy likelihood score. The trained model can be model 1100 as described above. The process 1200 can then proceed to 1216.

At 1224, the process 1200 can receive a malignancy likelihood score from the trained model. In some embodiments, the malignancy likelihood score can range from zero to one, inclusive, with one indicating a high risk of malignancy and zero indicating minimal or no risk of malignancy. In some embodiments, the malignancy can be a "yes" (i.e. 1) or "no" (i.e. 0), indicating if the tumor is predicted to be malignant or not malignant, respectively. In some embodiments, the malignancy likelihood score can indicate a category of risk, for example, a low risk, medium risk, or high risk category. In some embodiments, the malignancy likelihood score can be selected from a range of values, such as the integers 1-5, with 1 indicating a lowest risk level and 5 indicating a highest risk level. In some embodiments, the process 1200 can also receive one or more regions of interest generated by the trained model such as the regions of interest 1108 described above. The process 1200 can then proceed to 1220.

At 1228, the process 1200 can output the malignancy likelihood score to a memory for storage and/or use by another process, and/or to a display such as a computer monitor for viewing by a human practitioner. For example, the process 1200 can output the malignancy likelihood score to a display in a medical facility to allow a medical practitioner to view the malignancy likelihood score and potentially determine a diagnosis of a patient based on the malignancy likelihood score. The malignancy likelihood score may be stored in a database of medical records for future analysis and/or studies of breast cancer patients. In some embodiments, the process 1200 can also output one or more of the regions of interest received at 1216 for storage and/or use by another process, and/or to a display such as a computer monitor for viewing by a human practitioner. The process 1200 may output the malignancy likelihood score and/or the one or more regions of interest as a report. The process 1200 can then end.

It is understood that synthetic images generated using ROIs generated by either the model 200 or the model 900 can be used to generate malignancy likelihood scores using either the model 600 or the model 1100 described above. Thus, the disclosure provides systems and methods for efficiently and uniformly creating synthetic 2D images from 3D tomography data of a breast, as well as for estimating malignancy of tumors and/or lesions that may be present in the breast.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for determining a malignancy likelihood score for breast tissue of a patient, the method comprising:
  receiving a plurality of two-dimensional images of the breast tissue, the two-dimensional images being derived from a three-dimensional image of the breast tissue;
  providing each of the two-dimensional images to a first model comprising a first trained neural network that is trained to identify regions of interest; and
  receiving a first identified region of interest from the first model corresponding to a first image of the plurality of two-dimensional images;

receiving a second identified region of interest from the first model corresponding to a second image of the plurality of two-dimensional images;

generating a synthetic two-dimensional image by populating a pixel array of the synthetic two-dimensional image based on at least the first identified region of interest and the second identified region of interest;

providing the synthetic two-dimensional image to a second model comprising a second trained neural network;

receiving a malignancy likelihood score from the second model; and outputting a report including the malignancy likelihood score to at least one of a memory or a display.

2. The method of claim 1, comprising:

determining that the first region of interest and the second region of interest overlap;

determining that the first region of interest has a higher relevancy score than the second region of interest; and in response to determining the first region of interest has a higher relevancy score, including at least a portion of the first region of interest in the synthetic two-dimensional image.

3. The method of claim 2, wherein the first region of interest is associated with a first two-dimensional image included in the plurality of two-dimensional images and the second region of interest is associated with a second two-dimensional image included in the plurality of two-dimensional images.

4. The method of claim 1, wherein each of the first and second regions of interest comprises an array of pixels, each pixel comprising an intensity value, and a relevancy score.

5. The method of claim 4, wherein the generating comprises:

setting a first intensity value included in a first pixel included in the synthetic two-dimensional image equal to a second intensity value included in the first region of interest.

6. The method of claim 4, wherein the generating comprises:

setting a first intensity value included in a first pixel included in the synthetic two-dimensional image equal to a second intensity value included in a third two-dimensional image included in the plurality of two-dimensional images, the second intensity value being included in a second pixel not associated with any region of interest identified by the first model.

7. The method of claim 6, wherein the second third two-dimensional image is associated with at least one region of interest identified by the first model.

8. The method of claim 4, wherein the generating comprises:

determining a first coverage area associated with the first region of interest and comprising a second array of pixels;

determining a second coverage area associated with the second region of interest and comprising a third array of pixels; and determining a first intensity value of a first pixel included in the synthetic two-dimensional image based on a second intensity value included in the first coverage area and a third intensity value included in the second coverage area.

9. The method of claim 8, wherein the first coverage area includes at least one pixel not included in the first region of interest and the second coverage area includes at least one pixel not included in the second region of interest.

10. The method of claim 8, wherein the determining the first intensity value of the first pixel comprises:

setting the first intensity value equal to the sum of the second intensity value multiplied by a first weight plus the third intensity value multiplied by a second weight.

11. The method of claim 1, wherein the generating comprises:

determining that the first region of interest and the second region of interest overlap;

determining that the first region of interest has a higher relevancy score than the second region of interest; and in response to determining the first region of interest has a higher relevancy score, not including any portion of the second region of interest in the synthetic two-dimensional image.

12. The method of claim 1, wherein the three-dimensional image is generated using digital breast tomosynthesis.

13. The method of claim 1, wherein the first trained neural network comprises a first subnetwork, and the second trained neural network comprises a second subnetwork, the first subnetwork and the second subnetwork including the same number of layers and filters.

14. The method of claim 13, wherein the second trained neural network was trained using a set of weight values of the first neural network as initial weight values.

15. The method of claim 1 further comprising:

removing at least one region of interest from a number of regions of interest received from the first model; and generating a second synthetic two-dimensional image based on the number of regions of interest and at least one of the plurality of two-dimensional images.

16. The method of claim 1, wherein the first model is trained based on an image dataset comprising two-dimensional full-field digital mammography images annotated by a medical practitioner.

17. The method of claim 16, wherein each two-dimensional image included in the plurality of two-dimensional images of the breast tissue is a slice included in a three-dimensional digital breast tomosynthesis volume.

18. A system for determining a malignancy likelihood score for breast tissue of a patient, the system comprising:

a memory configured to store a plurality of two-dimensional images of the breast tissue, the two-dimensional images being derived from a three-dimensional image of the breast tissue;

a processor configured to access the memory and to:

provide each two-dimensional image to a first model comprising a first trained neural network that is trained to identify regions of interest;

receive a first identified region of interest from the first model corresponding to a first image of the plurality of two-dimensional images;

receive a second identified region of interest from the first model corresponding to a second image of the plurality of two-dimensional images;

generate a synthetic two-dimensional image by populating a pixel array of the synthetic two-dimensional image based on at least the first identified region of interest and the second identified region of interest;

provide the synthetic two-dimensional image to a second model comprising a second trained neural network;

determine a malignancy likelihood score using the second model; and a display configured to display a report including the malignancy likelihood score.

19. The system of claim 18, wherein, to generate the synthetic two-dimensional image, the processor is further to:
determine that the first region of interest and the second region of interest overlap;
determine that the first region of interest has a higher relevancy score than the second region of interest; and
in response to determining the first region of interest has a higher relevancy score, include at least a portion of the first region of interest in the synthetic two-dimensional image.

20. The system of claim 19, wherein the first region of interest is associated with a first two-dimensional image included in the plurality of two-dimensional images and the second region of interest is associated with a second two-dimensional image included in the plurality of two-dimensional images.

21. The system of claim 18, wherein each of the first and second regions of interest comprises an array of pixels, each pixel comprising an intensity value, and a relevancy score.

22. The system of claim 21, wherein, to generate the synthetic two-dimensional image, the processor is further to:
set a first intensity value included in a first pixel included in the synthetic two-dimensional image equal to a second intensity value included in the first region of interest.

23. The system of claim 21, wherein, to generate the synthetic two-dimensional image, the processor is further to:
set a first intensity value included in a first pixel included in the synthetic two-dimensional image equal to a second intensity value included in a third two-dimensional image included in the plurality of two-dimensional images, the second intensity value being included in a second pixel not associated with any region of interest identified by the first model.

24. The system of claim 21, wherein, to generate the synthetic two-dimensional image, the processor is further to:
determine a first coverage area associated with the first region of interest comprising a second array of pixels;
determine a second coverage area associated with the second region of interest and comprising a third array of pixels; and
determine a first intensity value of a first pixel included in the synthetic two-dimensional image based on a second intensity value included in the first coverage area and a third intensity value included in the second coverage area.

25. The system of claim 24, wherein the first coverage area includes at least one pixel not included in the first region of interest and the second coverage area includes at least one pixel not included in the second region of interest.

26. The system of claim 24, wherein, to determine the first intensity value of the first pixel, the processor is further to:
set the first intensity value equal to the sum of the second intensity value multiplied by a first weight plus the third intensity value multiplied by a second weight.

27. The system of claim 18, wherein, to generate the synthetic two-dimensional image, the processor is further to:
determine that the first region of interest and the second region of interest overlap;
determine that the first region of interest has a higher relevancy score than the second region of interest; and
in response to determining the first region of interest has a higher relevancy score, not include any portion of the second region of interest in the synthetic two-dimensional image.

28. The system of claim 18, wherein the three-dimensional image is generated using digital breast tomosynthesis and wherein each two-dimensional image included in the plurality of two-dimensional images of the breast tissue is a slice included in a three-dimensional digital breast tomosynthesis volume.

29. The system of claim 18, wherein the first trained neural network comprises a first subnetwork, and the second trained neural network comprises a second subnetwork, the first subnetwork and the second subnetwork including the same number of layers and filters, and wherein the second trained neural network was trained using a set of weight values of the first neural network as initial weight values.

30. A method for determining a malignancy likelihood score for breast tissue of a patient, the method comprising:
receiving a plurality of two-dimensional images of the breast tissue, the two-dimensional images being derived from a three-dimensional image of the breast tissue;
for each two-dimensional image:
providing the two-dimensional image to a first model comprising a first trained neural network; and
receiving a number of indicators from the first model, each indicator being associated with a two-dimensional image included in the plurality of two-dimensional images, wherein each indicator comprises an array of pixels, each pixel comprising an intensity value, and a relevancy score;
generating a synthetic two-dimensional image based on the number of indicators and at least one of the plurality of two-dimensional images, wherein the generating comprises:
determining a first coverage area associated with a first indicator included in the number of indicators and comprising a second array of pixels,
determining a second coverage area associated with a second indicator included in the number of indicators and comprising a third array of pixels, and
determining a first intensity value of a first pixel included in the synthetic two-dimensional image based on a second intensity value included in the first coverage area and a third intensity value included in the second coverage area;
providing the synthetic two-dimensional image to a second model comprising a second trained neural network;
receiving a malignancy likelihood score from the second model; and
outputting a report including the malignancy likelihood score to at least one of a memory or a display.

31. The method of claim 30, wherein the first coverage area includes at least one pixel not included in the first indicator and the second coverage area includes at least one pixel not included in the second indicator.

32. The method of claim 30, wherein the determining the first intensity value of the first pixel comprises:
setting the first intensity value equal to the sum of the second intensity value multiplied by a first weight plus the third intensity value multiplied by a second weight.

* * * * *

UNITED STATES PATENT AND TRADEMARK OFFICE
CERTIFICATE OF CORRECTION

| | |
|---|---|
| PATENT NO. | : 11,783,476 B2 |
| APPLICATION NO. | : 17/079957 |
| DATED | : October 10, 2023 |
| INVENTOR(S) | : William Lotter |

It is certified that error appears in the above-identified patent and that said Letters Patent is hereby corrected as shown below:

In the Specification

Column 26. Line 32, "11086" should be --1108B--.

Column 26. Line 33, "11086" should be --1108B--.

Signed and Sealed this
Twenty-third Day of January, 2024

Katherine Kelly Vidal
*Director of the United States Patent and Trademark Office*